US010593062B2

(12) United States Patent
Otani et al.

(10) Patent No.: US 10,593,062 B2
(45) Date of Patent: Mar. 17, 2020

(54) DEFECT OBSERVATION APPARATUS

(71) Applicant: HITACHI HIGH-TECHNOLOGIES CORPORATION, Minato-ku, Tokyo (JP)

(72) Inventors: Yuko Otani, Tokyo (JP); Kazuo Aoki, Tokyo (JP); Yohei Minekawa, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 227 days.

(21) Appl. No.: 15/386,262

(22) Filed: Dec. 21, 2016

(65) Prior Publication Data

US 2017/0249753 A1    Aug. 31, 2017

(30) Foreign Application Priority Data

Feb. 25, 2016    (JP) .................................. 2016-034706

(51) Int. Cl.
*G06T 7/80*        (2017.01)
*H04N 5/232*    (2006.01)
(Continued)

(52) U.S. Cl.
CPC ........... *G06T 7/80* (2017.01); *G01N 21/9501* (2013.01); *G01N 21/956* (2013.01); *G01N 23/2251* (2013.01); *G02B 21/0016* (2013.01); *G02B 21/06* (2013.01); *G02B 21/125* (2013.01); *G02B 21/365* (2013.01); *G03F 7/7065* (2013.01); *G06K 9/6202* (2013.01); *G06T 7/001* (2013.01); *G06T 7/74* (2017.01); *H04N 5/2256* (2013.01); *H04N 5/2354* (2013.01);
(Continued)

(58) Field of Classification Search
CPC ............ G01N 21/9501; G01N 21/956; G01N 2223/418; G01N 2223/6116; G01N 23/2251; G02B 21/0016; G02B 21/06; G02B 21/365; G03F 7/7065; G06K 9/6202; G06T 2207/10061; G06T 2207/30148; G06T 7/001; G06T 7/74; G06T 7/80; H04N 5/2256; H04N 5/23238; H04N 5/23245; H04N 5/23296; H04N 5/2354; H04N 7/181
USPC ........................................................ 348/79
See application file for complete search history.

(56) References Cited

U.S. PATENT DOCUMENTS

2003/0072481 A1*    4/2003    Wooten ................. G06T 7/0004
                                                                        382/145
2007/0194231 A1*    8/2007    Nakahira ................ H01J 37/28
                                                                        250/310
(Continued)

FOREIGN PATENT DOCUMENTS

JP        2007-235023 A            9/2007
JP        2015206642 A    *    11/2015    ............. G01B 11/30

*Primary Examiner* — James T Boylan
(74) *Attorney, Agent, or Firm* — Miles & Stockbridge, P.C.

(57) ABSTRACT

A defect observation apparatus includes a storage unit configured to store defect information about defects detected by an external inspection apparatus; a first imaging unit configured to capture an image of a defect using a first imaging condition and a second imaging condition; a control unit configured to correct positional information on the defect using the image captured with the first imaging unit; and a second imaging unit configured to capture an image of the defect based on the corrected positional information.

12 Claims, 14 Drawing Sheets

(51) Int. Cl.
*H04N 5/225* (2006.01)
*G02B 21/12* (2006.01)
*G03F 7/20* (2006.01)
*G06T 7/73* (2017.01)
*G01N 21/95* (2006.01)
*G01N 21/956* (2006.01)
*G01N 23/2251* (2018.01)
*G02B 21/00* (2006.01)
*G02B 21/06* (2006.01)
*G02B 21/36* (2006.01)
*G06K 9/62* (2006.01)
*G06T 7/00* (2017.01)
*H04N 5/235* (2006.01)
*H04N 7/18* (2006.01)

(52) U.S. Cl.
CPC ..... *H04N 5/23245* (2013.01); *H04N 5/23296* (2013.01); *H04N 7/181* (2013.01); *G01N 2223/418* (2013.01); *G01N 2223/6116* (2013.01); *G06T 2207/10061* (2013.01); *G06T 2207/30148* (2013.01); *H04N 5/23238* (2013.01)

(56) References Cited

U.S. PATENT DOCUMENTS

| | | | |
|---|---|---|---|
| 2008/0073524 A1* | 3/2008 | Nishiyama | G01N 23/225 250/307 |
| 2009/0002695 A1* | 1/2009 | Saito | G01N 21/8806 356/237.4 |
| 2009/0080759 A1* | 3/2009 | Bhaskar | G06T 7/001 382/141 |
| 2012/0023464 A1* | 1/2012 | Lin | G01N 21/8851 716/52 |
| 2013/0140457 A1* | 6/2013 | Minekawa | G06T 7/0004 250/307 |
| 2015/0286001 A1* | 10/2015 | Konno | G02B 6/2555 348/95 |
| 2017/0169554 A1* | 6/2017 | Karlinsky | G06T 7/001 |

\* cited by examiner

FIG. 1
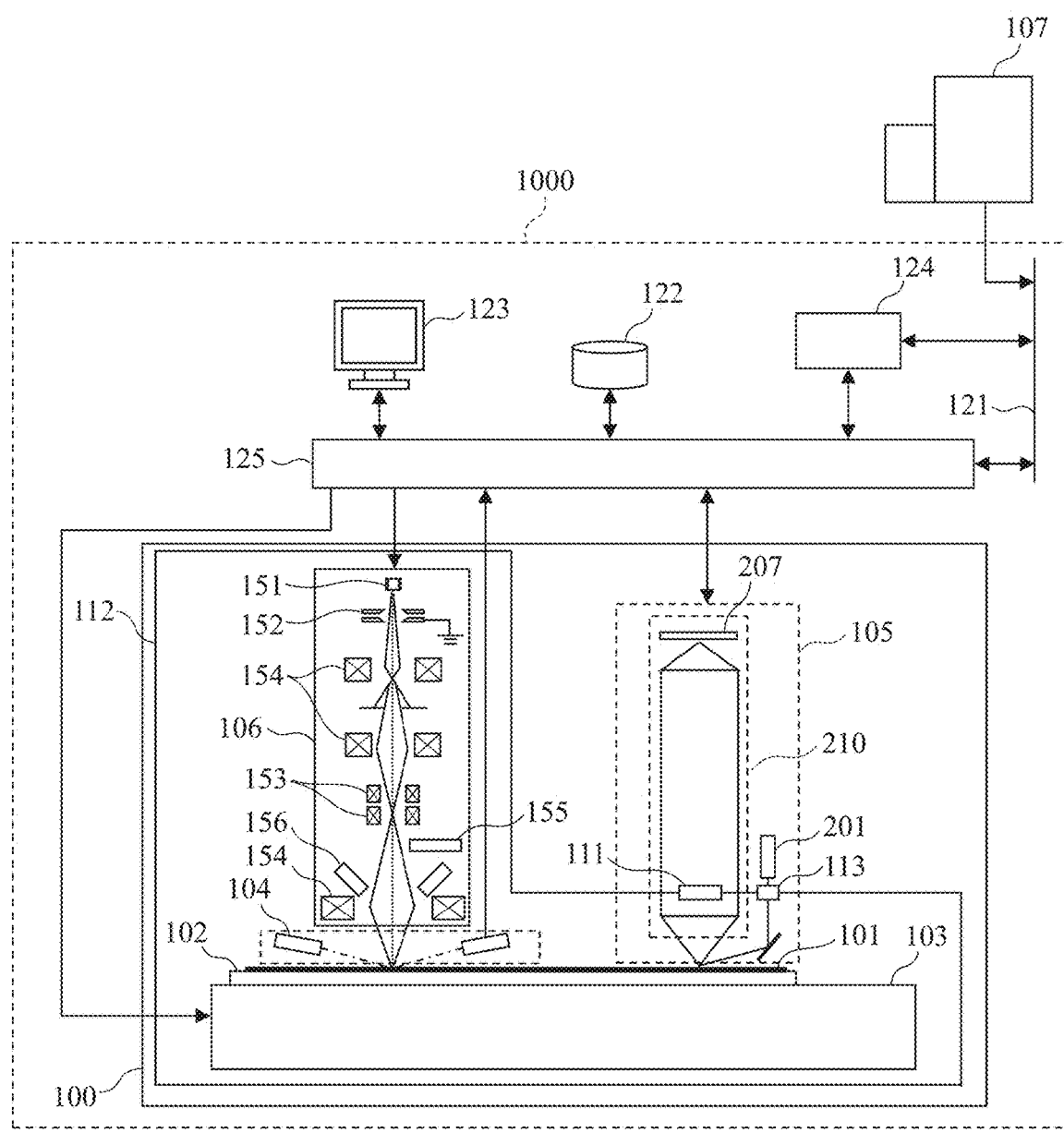
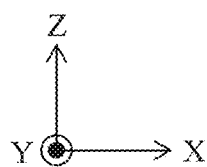

DEFECT OBSERVATION APPARATUS

CLAIM OF PRIORITY

The present application claims priority from Japanese patent application JP 2016-034706 filed on Feb. 25, 2016, the content of which is hereby incorporated by reference into this application.

BACKGROUND

Technical Field

The present invention relates to a defect observation apparatus.

Background Art

In the production processes of semiconductor devices, if foreign substances or pattern defects, such as breaking of wires and short circuits, (hereinafter, foreign substances and pattern defects shall be collectively referred to as "defects") are present on a wafer that is a semiconductor substrate, insulation failures of wires, short circuits of wires, and the like may occur. Such defects are mixed due to a variety of causes resulting from the production processes. Therefore, in order to mass-produce semiconductor devices, it is important to detect defects that are generated during a production process at an early stage, find out the source of generation of the defects, and thus prevent a decrease in yield.

A method for identifying a cause of generation of defects that is in widespread use will be described. First, the position of a defect on a wafer is identified using a defect inspection apparatus. Next, the defect is observed in detail with a SEM (Scanning Electron Microscope) or the like on the basis of the identified coordinate information on the defect. Then, a cause of generation of the defect is estimated through comparison of the result of observation with a database.

However, when such an identification method is used, there is a discrepancy between the coordinate system of the SEM and that of another inspection apparatus. Therefore, a defect that has been detected with another inspection apparatus is detected again with an optical microscope mounted on the SEM so that positional information (coordinate information) is corrected and the defect is observed in detail with the SEM on the basis of the corrected coordinate information. Accordingly, it is possible to correct the discrepancy between the two coordinate systems and thus improve the success rate of defect observation. For example, Patent Document 1 discloses a defect observation apparatus that includes an optical microscope and an electron microscope.

RELATED ART DOCUMENTS

Patent Documents

Patent Document 1: JP 2007-235023 A

SUMMARY

With an increase in the integration degree of semiconductor devices, the sizes of patterns that are formed on wafers have become smaller, and the sizes of defects that are fatal to the production of semiconductor devices have also become smaller correspondingly. With a decrease in the defect size, there is a possibility that the amount of reflected light/scattered light generated from the defects may decrease and thus may be buried in noise.

In view of the foregoing, in an optical microscope mounted on a SEM, the amount of scattered light from defects needs to be increased. As a method for increasing the amount of scattered light from defects, it may be effective to shorten the wavelength of illumination, increase the output level of illumination, increase the power density, increase the detection solid angle of detection optics, and increase the light exposure time of the detector.

However, increasing the power density by reducing the illumination spot size, for example, can narrow the field of view. When the illumination spot size of an optical microscope is reduced in order to detect defects with high sensitivity, a phenomenon may occur in which in the field of view does not contain defects, which can result in failures in the detection of defects.

Therefore, the present disclosure provides a technique for achieving both high-sensitivity detection and suppression of failures in defect detection in an optical microscope mounted on a SEM.

For example, configurations recited in the appended claims are adopted to solve the aforementioned problems. Although the present application includes a plurality of means for solving the aforementioned problems, there is provided, as an example, a defect observation apparatus including a storage unit configured to store defect information about a plurality of defects detected by an external inspection apparatus; a first imaging unit configured to capture an image of a defect among the plurality of defects using a first imaging condition and a second imaging condition, the first imaging condition being related to wide field-of-view imaging and the second imaging condition being related to narrow field-of-view imaging; a control unit configured to correct positional information on the defect using the image captured with the first imaging unit; and a second imaging unit configured to capture an image of the defect on the basis of the corrected positional information. The control unit is configured to set one of the first imaging condition or the second imaging condition for each of the plurality of defects, capture an image of a first-defect that is set to the first imaging condition, using the first imaging unit, calculate a correction formula on the basis of the defect information on the first-defect and positional information on the first-defect detected with the first imaging unit, correct positional information on a second-defect that is set to the second imaging condition, using the correction formula, and capture an image of the second-defect using the first imaging unit on the basis of the corrected positional information on the second-defect.

As another example, there is also provided a defect observation apparatus including a storage unit configured to store defect information about a plurality of defects detected by an external inspection apparatus; a first imaging unit configured to capture an image of a defect corresponding to a specified defect ID; a control unit configured to correct positional information on the defect using the image captured with the first imaging unit; and a second imaging unit configured to capture an image of the defect on the basis of the corrected positional information. The control unit is configured to, when the image captured with the first imaging unit contains a plurality of defects, extract, from the defect information, candidate defects that are possibly contained in the captured image, identify, in the captured image, the defect corresponding to the defect ID on the basis of a relative relationship between the candidate defects and a relative relationship between the plurality of defects contained in the captured image, and correct positional information on the defect corresponding to the defect ID.

According to the present invention, it is possible to achieve both high-sensitivity detection and suppression of failures in defect detection in an optical microscope mounted on a SEM. Further features associated with the present invention will become apparent from the description of the present specification and the accompanying drawings. In addition, other problems, configurations, and advantages will become apparent from the following description of embodiments.

BRIEF DESCRIPTION OF THE DRAWINGS

FIG. 1 is a block diagram showing the overall configuration of a defect observation apparatus in Embodiment 1 of the present invention.

DETAILED DESCRIPTION

Figure 2:
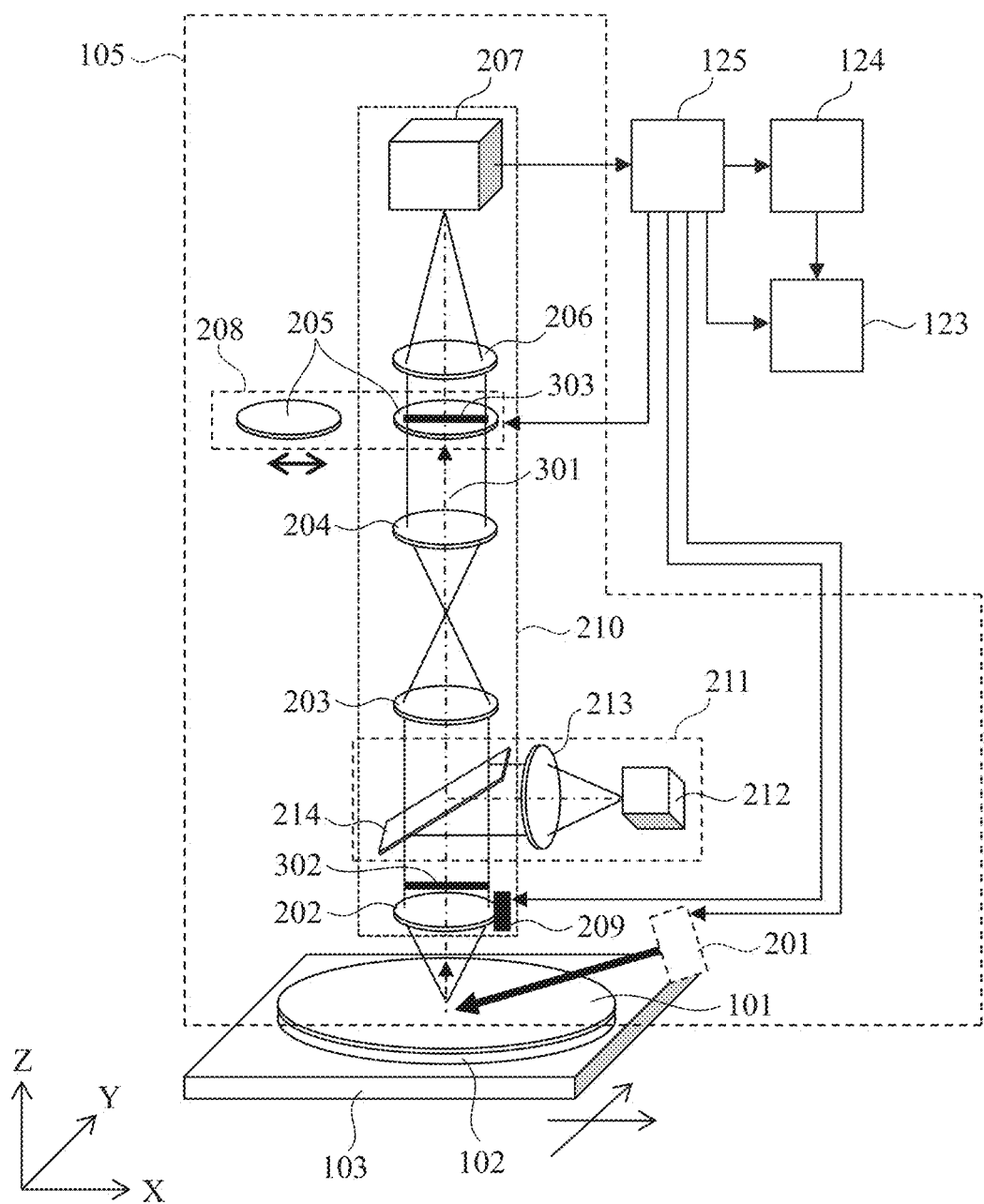
FIG. 2 is a schematic configuration diagram of an optical microscope unit of a defect observation apparatus in Embodiment 1 of the present invention.

Hereinafter, embodiments of the present invention will be described with reference to the accompanying drawings. Although the drawings illustrate specific embodiments in accordance with the principle of the present invention, such drawings should be used only for the understanding of the present invention and not for narrowly construing the present invention.

The following embodiments relate to a defect observation apparatus for observing defects and the like generated on a semiconductor wafer during a production process of a semiconductor device, at high speed and with high resolution, and a method for observing defects using such an apparatus.

Embodiment 1

FIG. 1 is a configuration diagram of a defect observation apparatus in Embodiment 1. A defect observation apparatus 1000 mainly includes a reviewing device 100, a network 121, a database 122, a user interface 123, a storage device 124, and a control unit 125.

The defect observation apparatus 1000 is connected to a defect inspection apparatus 107, which is an external inspection apparatus, over the network 121. The defect inspection apparatus 107 detects defects on a sample 101 and acquires defect information. The defect information is information about a plurality of defects on the sample 101, and includes information such as a defect ID of each defect, the position coordinates of each defect, and the size of each defect. The defect inspection apparatus 107 may be any device as long as it can acquire information about defects on the sample 101.

The control unit 125 and the storage device 124 are connected to the defect inspection apparatus 107 over the network 121. Defect information acquired by the defect inspection apparatus 107 is input to the storage device 124 or the control unit 125 via the network 121. The storage device 124 stores defect information that is input from the defect inspection apparatus 107 via the network 121. The control unit 125 reads the defect information input from the defect inspection apparatus 107 or the defect information stored in the storage device 124, and controls the reviewing device 100 on the basis of the read defect information. The control unit 125 observes some or all of the defects detected by the defect inspection apparatus 107 in detail using the reviewing device 100. The control unit 125 classifies the defects or analyzes the source of generation of the defects by comparing the results of observation with information in the database 122.

Next, the configuration of the reviewing device 100 shown in FIG. 1 will be described. The reviewing device 100 includes a drive portion having a sample holder 102 and a stage 103; an optical height detector 104; an optical microscope unit 105; a vacuum chamber 112 with vacuum-sealed windows 111 and 113; a SEM 106 (electron microscope unit); and a laser displacement meter (not shown).

The sample holder 102 is placed on the movable stage 103. The sample 101 is placed on the sample holder 102. The stage 103 moves the sample 101, which is placed on the sample holder 102, between the optical microscope unit 105 and the SEM 106. With the movement of the stage 103, the defect to be observed on the sample 101 can be placed within the field of view of the SEM 106 or the field of view of the optical microscope unit 105.

The control unit 125 is connected to the stage 103, the optical height detector 104, the optical microscope unit 105, the SEM 106, the user interface 123, the database 122, and the storage device 124. The control unit 125 controls the operation of each component and input and output. For example, the control unit 125 controls the (i) movement of the stage 103, (ii) modulation of the illumination state of the optical microscope unit 105, lens configuration, and image acquisition conditions, (iii) image acquisition with the SEM 106 and acquisition conditions therefor, (iv) measurement with the optical height detector 104 and measuring conditions therefor, and the like.

The optical height detector 104 measures a value in accordance with a displacement of the surface of the region to be observed. The displacement herein includes a variety of parameters, such as the position of the region to be observed, the amplitude of vibration, the frequency of vibration, and the period of vibration. Specifically, the optical height detector 104 measures the height position of the surface of the region to be observed of the sample 101 on the stage 103, and vibration in the perpendicular direction with reference to the surface of the region to be observed. The optical height detector 104 outputs the measured displacement and vibration as a signal to the control unit 125. Information on the measured displacement and vibration is fed back to the movement sequence of the stage 103.

FIG. 2 shows the configuration of the optical microscope unit 105. The optical microscope unit 105 includes dark-field illumination optics 201, bright-field illumination optics 211, and detection optics 210. In FIG. 2, the vacuum chamber 112 and the vacuum-sealed windows 111 and 113 are omitted.

Figure 3:
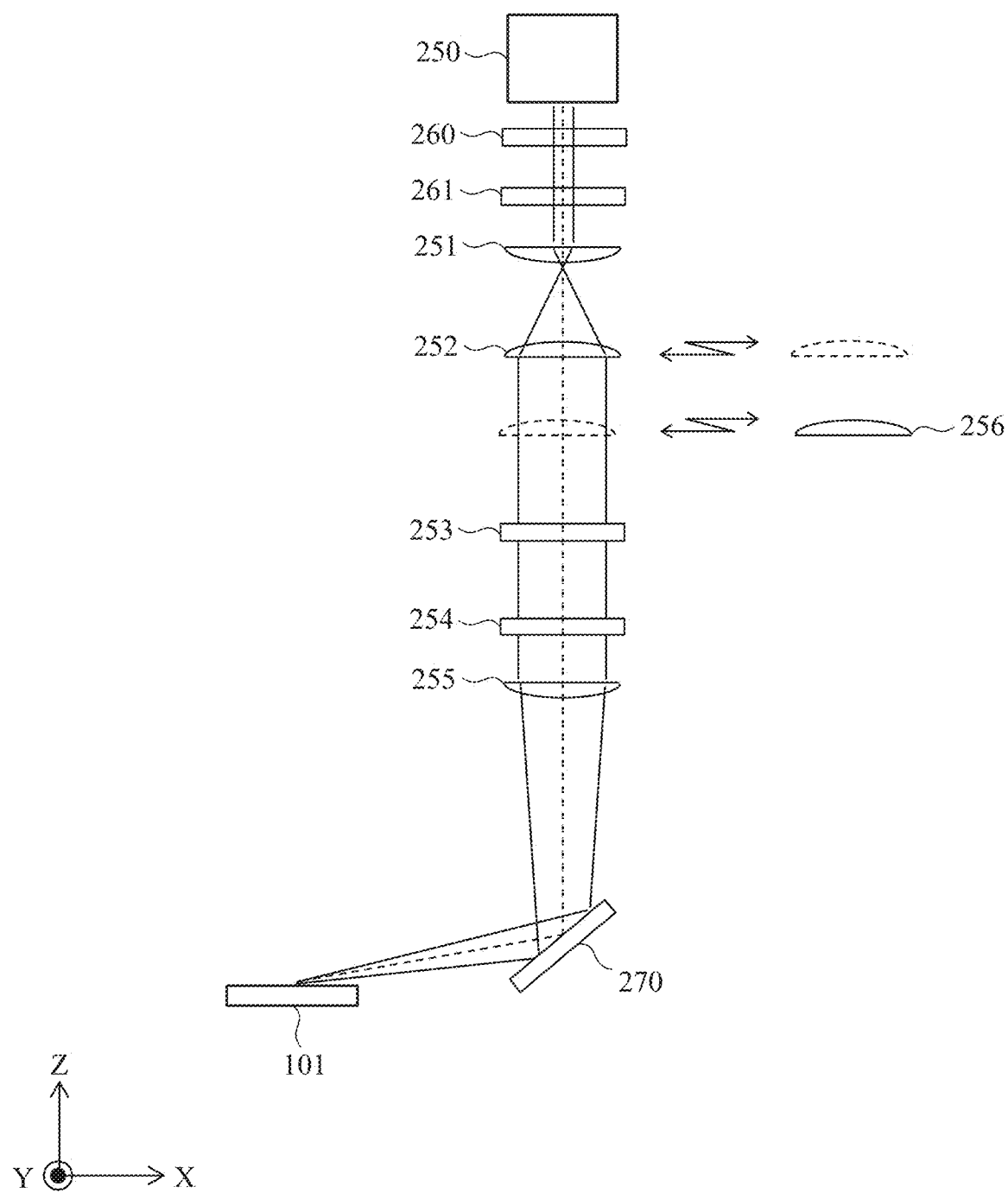
FIG. 3 is a schematic configuration diagram of illumination optics of an optical microscope unit in Embodiment 1 of the present invention.

FIG. 3 shows the schematic configuration of the dark-field illumination optics 201. The dark-field illumination optics 201 include a light source 250, plano-convex lenses 251 and 252, cylindrical lenses 253 and 254, a condensing lens 255, a ½ wave plate 260, and an ND filter 261.

A laser beam emitted from the light source 250 is converted into a collimated beam with a larger beam diameter through the plano-convex lenses 251 and 252. Further, the diameter of the laser beam is reduced only in the Y-axis direction through the cylindrical lenses 253 and 254. Then, the laser beam is focused via the condensing lens 255, and is allowed to become incident on the sample 101 as an approximately circular spot. At this time, the laser beam is allowed to become incident on the sample 101 at an elevation angle of 10 degrees using a mirror 270.

Herein, the plano-convex lens 252 can be replaced with a plano-convex lens 256 with a different focal length in response to an instruction from the control unit 125. Each of the plano-convex lenses 252 and 256 is provided with a drive mechanism (not shown). With the drive mechanisms, the lens can be replaced. In addition, the plano-convex lens 256 is arranged at a position in accordance with the focal length so that a laser beam having passed through the plano-convex lens 256 becomes a collimated beam. Accordingly, the laser beam spot diameter can be changed without changing the center position of the laser beam spot that irradiates the sample 101. Although FIG. 3 illustrates an example in which the components of from the light source 250 to the condensing lens 255 are aligned, it is also possible to use a configuration in which a laser beam from the light source 250 is folded back using a mirror as appropriate.

Rotating the ½ wave plate 260 can adjust the polarization of a laser beam. In addition, the laser power can be adjusted by the ND filter 261. The rotation angle of the ½ wave plate 260 and the transmissivity of the ND filter 261 can be controlled by the control unit 125.

Although this embodiment illustrates an example in which the illumination spot is changed by replacing the plano-convex lens 252 with a lens with a different focal length, the method for changing the illumination spot is not limited to replacing the plano-convex lens. For example, the illumination spot may be changed by changing the distance between the lenses. Accordingly, the number of lenses and lens drive mechanisms can be reduced, thus saving space.

Although this embodiment illustrates an example in which a lens to be used is selected between two lenses with different focal lengths, the number of lenses used is not limited to two. For example, it is also possible to prepare another lens with a shorter focal length and select a lens to be used among the three lenses. When the lens is replaced with the lens with a shorter focal length, it is possible to form a further wider illumination spot. Therefore, failures in the detection of defects can be suppressed.

In addition, the wavelength of the light source, illumination elevation angle, the number of lenses, and the arrangement of lenses are not limited to those described in this embodiment, either.

As shown in FIG. 2, the bright-field illumination optics 211 include a white light source 212, an illumination lens 213, a half mirror 214, and an objective lens 202. A white illumination beam emitted from the white light source 212 is converted into a collimated beam by the illumination lens 213. Then, a half of the collimated beam that has become incident on the half mirror 214 is folded back in a direction parallel with the optical axis of the detection optics 210. Further, the beam folded back by the half mirror 214 is focused onto and irradiate the region to be observed by the observation lens 202.

As the half mirror 214, it is possible to use a dichroic mirror that can pass more scattered light toward the detector 207. In addition, it is also possible to use a configuration in which the bright-field illumination optics 211 are not selected to be used so that more scattered light, which has been generated from the surface of the sample 101 by the illumination by the dark-field illumination optics 201, can reach the detector 207. In such a case, the bright-field illumination optics 211 may have a configuration in which the half mirror 214 is removable from the optical axis 301.

As shown in FIG. 2, the detection optics 210 include the objective lens 202, lenses 203 and 204, a spatially distributed optical element 205, an imaging lens 206, and the detector 207. With the illumination by the dark-field illumination optics 201 or the bright-field illumination optics 211, reflected light and/or scattered light generated from the illuminated region on the sample 101 are/is focused by the objective lens 202, thus forming an image on the detector 207 via the lenses 203 and 204 the imaging lens 206. The imaged light is converted into an electric signal by the detector 207, and the electric signal is output to the control unit 125. The signal processed by the control unit 125 is stored in the storage device 124. In addition, the stored processing results are displayed via the user interface 123.

The spatially distributed optical element 205 is arranged on a pupil plane 302 of the detection optics 210 or on a pupil plane 303 on which an image is formed by the lenses 203 and 204. The spatially distributed optical element 205 controls light shielding with a mask or controls the polarization direction of a light beam passing therethrough with respect to a light beam focused by the objective lens 202. Examples of the spatially distributed optical element 205 include a filter that passes only a light beam polarized in the X-axis direction, a filter that passes only a light beam polarized in the Y-axis direction, and a filter that passes only a polarized light beam vibrating in the radial direction about the optical axis 301 as the center. Alternatively, the spatially distributed optical element 205 may be a filter that is masked so as to cut out scattered light generated due to the surface roughness of the sample 101 or a filter whose transmission/polarization direction is controlled so as to cut out scattered light generated due to the surface roughness of the sample 101.

The detection optics 210 may also include a switching mechanism 208 for switching among a plurality of spatially distributed optical elements 205 with different optical properties. The switching mechanism 208 arranges a spatially distributed optical element 205, which is suitable for detection of the target defect among the plurality of spatially distributed optical elements 205, on the optical axis 301 of the detection optics 210. The spatially distributed optical element 205 need not necessarily be arranged on the optical axis 301. In such a case, a dummy substrate that changes the optical path length by the same amount as that of the spatially distributed optical element 205 is arranged on the optical axis 301. The switching mechanism 208 can also switch among the spatially distributed optical elements 205 and the dummy substrate. For example, when bright-field observation is performed or when there is no spatially distributed optical element 205 that is suitable for observing a target, there is a possibility that an image acquired by the detector 207 may become distorted due to the spatially distributed optical element 205. Therefore, the dummy substrate may be arranged on the optical axis 301 when the spatially distributed optical element 205 is not used.

A height control mechanism 209 is used to allow the surface to be observed on the sample 101 to coincide with the focal position of the detection optics 210 in response to an instruction from the control unit 125. As the height control mechanism 209, a linear stage, an ultrasonic motor, piezoelectric stage, or the like can be used.

As the detector 207, a two-dimensional CCD sensor, a line CCD sensor, a TDI sensor group having a plurality of TDIs arranged in parallel, a photo diode array, or the like can be used. In addition, the sensor surface of the detector 207 is arranged so as to be conjugate to the surface of the sample 101 or the pupil plane of the objective lens 202.

When the illumination spot is changed by the dark-field illumination optics 201, the size of an image formed on the detector 207 also becomes smaller. In such a case, pixels of the detector 207 to be used may be limited to a pixel region that has the center of the detector as the center. For example, when the illumination spot diameter is reduced to ½, only ¼ of the entire pixels of the detector 207 may be cut out. Accordingly, the volume of data to be transferred or stored can be reduced.

When the pixel region of the detector 207 is cut out, it is possible to measure the position of the stage 103 using a laser displacement meter (not shown), and feed back the results of measurement so as to change the region to be cut out. Typically, the stopping accuracy of the stage 103 is lower than the measurement accuracy of the laser displacement meter. Thus, when the stage 103 is displaced from a desired stop position by +10 μm in the X-axis direction, for example, it is acceptable as long as the range of the pixels to be cut out is shifted by +10 μm in the X-axis direction.

When the illumination spot is changed by the dark-field illumination optics 201, it is also possible to change the distance between the lenses 203 and 204 without cutting out the pixel region of the detector 207. With the distance between the lenses changed, the optical magnification of the entire detection optics 210 is changed and adjustment is thus achieved such that a region imaged by the detector 207 approximately coincides with the illumination spot. As another example, it is also possible to change the optical magnification of the entire detection optics 210 by replacing the objective lens 202 with another objective lens with a different magnification. According to such a configuration, adjustment is achieved such that a region imaged by the detector 207 approximately coincides with the illumination spot. As a further alternative example, the aforementioned two means may be combined to change the magnification. Accordingly, it becomes possible to adjust the pixel size to an optimal size in accordance with the illumination spot diameter.

The control unit 125 reads defect information output from the defect inspection apparatus 107 or defect information stored in the storage device 124, and controls the stage 103 on the basis of the read defect information so that the field of view of the optical microscope unit 105 contains the defect(s) to be observed. Then, the control unit 125 calculates a deviation between the defect coordinates of the defect inspection apparatus 107 and the defect coordinates of the reviewing device 100 on the basis of the image detected with the optical microscope unit 105, and corrects the defect coordinate information stored in the storage device 124.

The SEM 106 includes an electron irradiation unit and an electron detection unit. The electron irradiation unit includes an electron beam source 151, an extracting electrode 152, a deflecting electrode 153, and an objective lens electrode 154. In addition, the electron detection unit includes a secondary electron detector 155 and a reflected electron detector 156. It should be noted that the SEM 106 may also include, in addition to such components, other lenses, electrodes, and detectors, and may also have a partially different configuration from that described above. That is, the configuration of the SEM is not limited thereto.

Primary electrons are emitted from the electron beam source 151 of the SEM 106, and the emitted primary electrons are extracted in a beam form by the extracting electrode 152, and then are accelerated. Then trajectory of the primary electron beam accelerated by the deflecting electrode 153 is controlled in the X-direction and the Y-direction. Herein, two axes of a plane that is orthogonal to the primary electron beam are referred to as an X-direction and a Y-direction, and a direction of an axis that is parallel with the primary electron beam is referred to as a Z-direction.

The primary electron beam with the controlled trajectory is converged on the surface of the sample 101 by the objective lens electrode 154, and the surface of the sample 101 is thus scanned with the converged beam. Secondary electrons and/or reflected electrons and the like are generated from the surface of the sample 101 irradiated and scanned with the primary electron beam. The secondary electron detector 155 defects the generated secondary electrons, and the reflected electron detector 156 detects electrons with relatively high energy, such as reflected electrons.

A shutter (not shown) arranged on the optical axis of the SEM 106 is used to select the start or stop of the irradiation of the sample 101 with an electron beam emitted from the electron beam source 151. The measurement conditions of the SEM 106 are controlled by the control unit 125. The control unit 125 can change the acceleration voltage, electron beam focus, and observation magnification. The SEM 106 observes defects in detail on the basis of the defect coordinate information that has been corrected using the image captured with the optical microscope unit 105.

Figure 4:
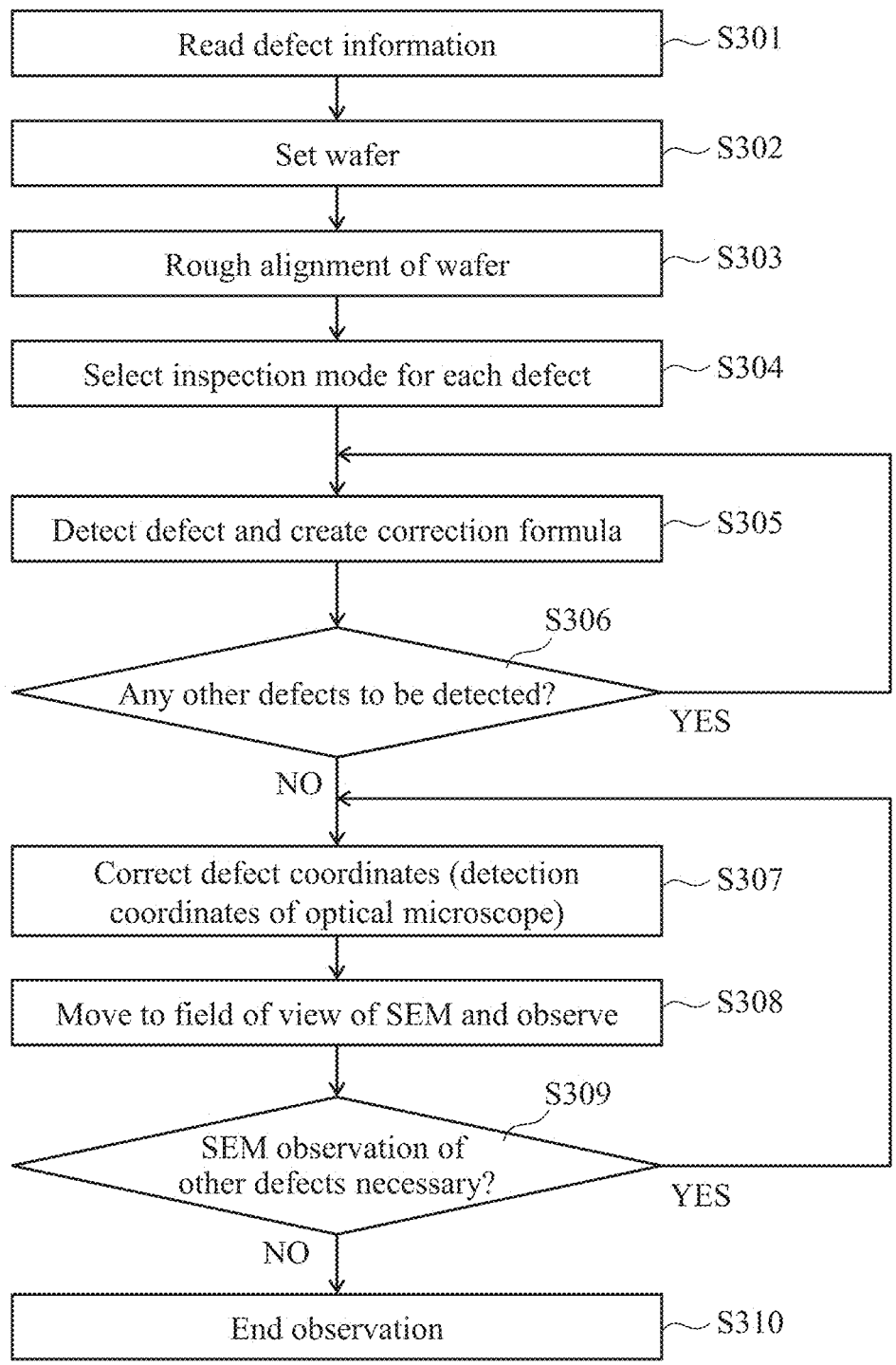
FIG. 4 is a flowchart showing a flow of a defect observation process in Embodiment 1 of the present invention.
Figure 5:
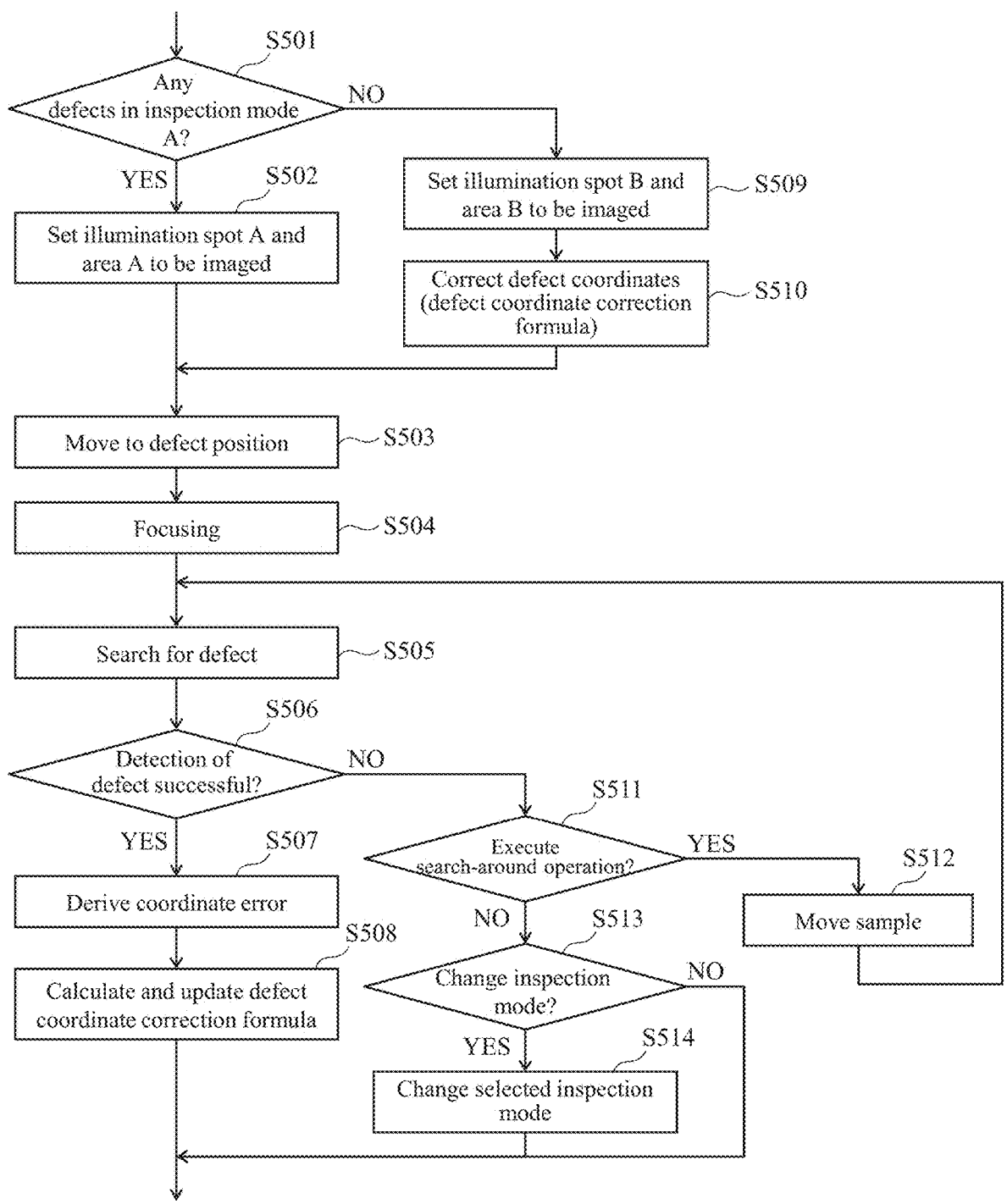
FIG. 5 is a flowchart showing a detailed flow of a defect detection and correction formula creation step in FIG. 4.

FIG. 4 is a flowchart showing a flow of the defect observation process in this embodiment. FIG. 5 is a flowchart showing a detailed flow of a defect detection and correction formula creation step in FIG. 4. First, the flow in FIG. 4 will be described.

(Step S301)

The control unit 125 reads information on defects on a wafer to be observed. Specifically, the control unit 125 reads defect information output from the defect inspection apparatus 107 or defect information stored in the storage device 124. Examples of the defect information include defect inspection results including one or more of a defect ID, defect coordinates, defect signal, defect size, defect shape, a polarized light beam of scattered light from a defect, defect type, defect label, luminance, bright spot area, and defect feature quantity of a defect detected with the defect inspection apparatus 107, and a signal of scattered light from the surface of the sample 101; and defect inspection conditions including one or more of an illumination incident angle, illumination wavelength, illumination azimuth, illumination intensity, and illumination polarization of the defect inspection apparatus 107, the azimuth and elevation angle of the detector, and a detection region of the detector 207. When the defect inspection apparatus 107 includes a plurality of detectors and the defect inspection apparatus 107 outputs defect information detected with the plurality of detectors, the control unit 125 may use defect information on the sample 101 for each detector, or use defect information detected with the plurality of detectors by combining them. In addition, the control unit 125 may use a feature quantity derived on the basis of the aforementioned defect information. The feature quantity is information representing the likelihood of a defect. The feature quantity may include not only information representing the feature of a detected signal obtained from the detector but also information representing a feature obtained by executing a predetermined process on the detected signal.

(Step S302)

The wafer to be observed is fixed on the sample holder 102.

(Step S303)

The control unit 125 executes rough alignment. The control unit 125 may irradiate the sample 101 with a light beam using the bright-field illumination optics 211 of the optical microscope unit 105, and perform rough alignment on the basis of an image obtained with the detection optics 210. As another example, the control unit 125 may perform rough alignment on the basis of an image obtained with another microscope for alignment (not shown) mounted on the defect observation apparatus 1000.

(Step S304)

Next, the control unit 125 selects an inspection mode for each defect on the basis of the defect information read in S301. In this step, an inspection mode is initially set for each detect. Examples of the inspection mode include a high-sensitivity mode (narrow-field mode) in which inspection is performed with a narrow illumination spot so as to detect defects with high sensitivity, and a wide-field mode in which inspection is performed with a wide illumination spot so as to suppress failures in the detection of defects.

The first selection example of the inspection mode will be described. For example, the high-sensitivity mode may be selected for a defect whose defect size included in the defect information read in S301 is small and that is thus determined to be difficult to be detected in the wide-field mode, while the wide-field mode may be selected for other defects to avoid failures in the detection.

The second selection example of the inspection mode will be described. For example, the entire wafer surface is split into a plurality of regions, and defects in the split regions are sorted in order of increasing or decreasing evaluation value. The control unit 125 may select the wide-field mode for N (which may be any number) defects in order of decreasing (or increasing) evaluation value, and select the high-sensitivity mode for other defects. The evaluation value may be calculated from at least one of the defect coordinates, defect size, defect type, size difference from a neighboring defect, the number of neighboring defects, or the like included in the defect information read in S301.

The third selection example of the inspection mode will be described. When there is a large number of defects around a given defect and there is thus a high possibility that a plurality of defects may be contained in the same field of view, which may result in erroneous selection of a defect, the high-sensitivity mode may be selected for such defect.

The fourth selection example of the inspection mode will be described. When there is a great difference in luminance between a given defect and a neighboring defect and there is thus a possibility that the defect may be buried in an image of the neighboring defect, stray light derived from the neighboring defect, or the like in the wide-field mode, the high-sensitivity mode may be selected for such defect.

The fifth selection example of the inspection mode will be described. If it is predicted to be difficult to detect all or many of the defects to be observed on the sample 101 in the wide-field mode from the defect information read in S301, the control unit 125 may select the high-sensitivity mode for all of the defects. In such a case, the control unit 125 may change the order of observation of the defects as follows. For example, the control unit 125 may preferentially capture images of defects that are predicted to have high coordinate accuracy. As another example, the control unit 125 may capture images of defects such that the entire wafer surface is uniformly sampled. Examples of defects that are predicted to have high coordinate accuracy include foreign substances. To the contrary, examples of defects with low coordinate accuracy include scratches.

It should be noted that when the high-sensitivity mode is selected, the control unit 125 may also select the high-sensitivity detection conditions for the optical microscope unit 105. For example, when the high-sensitivity mode is selected, the control unit 125 may control the spatially distributed optical element 205 to be arranged on the optical axis of the detection unit.

The sixth selection example of the inspection mode will be described. A user may specify an inspection mode. For example, the control unit 125 may select an inspection mode that has been input using the user interface 123.

The seventh selection example of the inspection mode will be described. The control unit 125 may select an inspection mode on the basis of design data. For example, the control unit 125 may determine whether the gap between wires is short from design data on the wafer. In such a case, as there is a high possibility that the size of a defect that is fatal may be small, the control unit 125 selects the high-sensitivity mode. Meanwhile, if the size of a defect that is fatal is large, the control unit 125 selects the wide-field mode to suppress failures in the detection of defects.

(Step S305)

Next, the control unit 125 detects a defect with the optical microscope unit 105 using the selected inspection mode, and creates a defect coordinate correction formula. The detailed flow of S305 will be described later with reference to FIG. 5. The control unit 125 can derive a coordinate error from the imaged defect, and create and update the defect coordinate correction formula from the derived coordinate error. According to such a configuration, the number of times of search-around operation to be executed can be reduced once the accuracy of the defect coordinate correction formula is ensured.

(Step S306)

Next, the control unit 125 determines whether there remain other defects to be observed. If there remain other defects to be observed (YES), the flow returns to S305, and a similar process is performed on the remaining target defects. Upon completion of detection of all defects (or defects specified by a user) (NO), the flow proceeds to S307.

(Step S307)

Next, the control unit 125 corrects the defect coordinates (coordinate information acquired by the defect inspection apparatus 107) read in S301, using the defect coordinate correction formula calculated in S305.

(Step S308)

Next, the control unit 125 moves the stage 103 so that the field of view of the SEM 106 contains the defect(s) on the basis of the defect coordinates corrected in S307. Then, the control unit 125 acquires a SEM image using the SEM 106.

(Step S309)

Next, the control unit 125 determines whether there remain other defects to be observed with the SEM. If there remain other defects to be observed (YES), the flow returns to S307. After that, the control unit 125 acquires coordinate information on a next defect to be observed, and repeatedly executes SEM observation. Upon completion of SEM observation of all defects (or defects specified by the user (NO)), defect observation by the reviewing device 100 terminates (S310).

Next, the flow in FIG. 5 will be described. FIG. 5 is a flowchart showing a detailed flow of the defect detection and correction formula creation step (S305) in FIG. 4.

(Step S501)

The control unit 125 determines whether the plurality of defects to be observed include defects in the inspection mode A. Herein, the inspection mode A is the wide-field mode. If it is determined that there are defects in the inspection mode A, the flow proceeds to S502 and observation is executed on the defects in the inspection mode A. Therefore, defect detection in the inspection mode A is continuously executed until detection of all defects set in the wide-field mode (inspection mode A) is completed. Meanwhile, if there is no defect in the inspection mode A (that is, upon completion of detection of defects in the inspection mode A), the flow proceeds to S509. Hereinafter, a flow when there are defects in the inspection mode A will be described. An illumination spot and an area to be imaged that are set in the inspection mode A shall be referred to as an illumination spot A and an area A to be imaged, respectively.

(Step S502)

The control unit 125 sets the observation conditions for the inspection mode A. The control unit 125 sets the illumination spot A by changing the lens configuration and arrangement of the dark-field illumination optics 201. Along with this, the control unit 125 limits the pixels to be used by the detector 207 (selects the area A to be imaged) when cutting out the pixels of the detector 207. In addition, the control unit 125 also sets parameters that are necessary for imaging, such as the illumination laser power, polarization, and detection time.

(Step S503)

The control unit 125 moves the stage 103 so that the field of view of the optical microscope unit 105 contains the defect to be observed on the basis of the defect information read in S301. It should be noted that after the first defect is detected, a defect coordinate correction formula is created in S508 described below. Therefore, for detection of defects following the first defect, the control unit 125 corrects the defect information read in S301 using the defect coordinate correction formula, and moves the stage 103 so that the field of view of the optical microscope unit 105 contains the defect to be observed. Accordingly, the frequency of failures in the detection of defects can be reduced.

(Step S504)

The control unit 125 adjusts the height of the objective lens 202 of the optical microscope unit 105 using the height control mechanism 209, and also adjusts the height of the stage 103 so that the focal point of the optical microscope unit 105 coincides with the surface of the sample 101. In focusing, the control unit 125 performs laser irradiation using the dark-field illumination optics 201, and acquires a plurality of images while changing the height of the objective lens 202 and/or the height of the stage 103. The control unit 125 calculates feature quantities (e.g., defect area and maximum luminance value) from the plurality of images. For example, when a defect area is used as the evaluation value for focusing, a point image of a defect has the minimum area when it is in focus. Therefore, a condition where a defect area is minimum is regarded as "just focus." As another example, when the maximum luminance value is used as the evaluation value, a point image of a defect has the maximum luminance value when it is in focus. Therefore, a condition where the luminance value is maximum is regarded as "just focus." In addition, the control unit 125 may integrate the aforementioned area and luminance value and calculate the just focus position from the integrated evaluation value.

(Step S505)

The control unit 125 captures an image of a region around the defect to be observed using the optical microscope unit 105, and searches for the defect in the acquired image.

(Step S506)

The control unit 125 determines whether the defect to be observed has been detected from the image acquired in S505. If detection of the defect is successful (YES), the flow proceeds to S507. Meanwhile, if detection of the defect fails (NO), the flow proceeds to S511.

(Step S507)

The control unit 125 calculates error data between the coordinate information calculated by the optical microscope unit 105 and the coordinate information output from the defect inspection apparatus 107. For example, the error calculated herein is an error of the position of the center of gravity of the defect image.

(Step S508)

The control unit 125 calculates a defect coordinate correction formula for converting the defect information output from the defect inspection apparatus 107 into a defect on the defect observation apparatus 1000, using the error data calculated in S507. The defect coordinate correction formula calculated herein is used in moving to a next defect position (S503 and S510).

When the first defect is detected, a new defect coordinate correction formula is created. However, when the second and following defects are detected, the control unit 125 updates the defect coordinate correction formula on a timely basis each time error data is obtained in S507. Accordingly, each time a search for defects (S505) and defect detection (S506) are performed, the accuracy of the defect coordinate correction formula can be improved. It should be noted that the control unit 125 may terminate updating the defect coordinate correction formula when the error data calculated in S507 has become less than a given threshold.

It should be noted that when the reliability of the error data calculated in S507 is low (e.g., when error data is calculated from defect coordinate data with low coordinate accuracy), the control unit 125 need not use the error data for updating the defect coordinate correction formula. This is because there is a possibility that the accuracy of the defect coordinate correction formula may decrease.

(Step S511)

If no defects are detected in S506, it is considered that the field of view does not contain defects. Therefore, the control unit 125 determines whether to perform a search-around operation (searching a portion around the first imaged region) or not. If the search-around operation is performed, the flow proceeds to S512. Meanwhile, if the search-around operation is not performed, the flow proceeds to S513.

(Step S512)

If the search-around operation is performed, the control unit 125 moves the stage 103 in the horizontal direction (X-direction and Y-direction) by a distance corresponding to the field of view of the optical microscope unit 105. After that, the flow returns to S505 so that imaging and a search for defects are performed in the new field of view.

(Step S513)

If the search-around operation is not performed, the control unit 125 determines whether to change the inspection mode or not. If it is determined that the inspection mode should be changed (YES), the flow proceeds to S514. Meanwhile, if detection of defects is abandoned, the inspection mode is not changed (NO).

(Step S514)

The control unit 125 changes the initial inspection mode selected in S304 to another inspection mode.

(Step S509)

If no defects in the inspection mode A are found in step S501 (that is, if correction of coordinate errors of defects in the inspection mode A is complete), the control unit 125 sets the observation conditions for the inspection mode B. Herein, the inspection mode B is the high-sensitivity mode. Defects in the inspection mode B include defects that have been initially set in the inspection mode B and defects that have been initially set in the inspection mode A, but the inspection mode of which has been changed later as the defects have not been detected (S514). Hereinafter, an illumination spot and an area to be imaged that are set in the inspection mode B shall be referred to as an illumination spot B and an area B to be imaged, respectively. The control unit 125 sets the illumination spot B by changing the lens configuration and arrangement of the dark-field illumination optics 201. Along with this, the control unit 125 limits the pixels to be used by the detector 207 when cutting out the pixels of the detector 207 (selects the area B to be imaged). In addition, the control unit 125 sets parameters that are necessary for imaging, such as the illumination laser power, polarization, and detection time.

(Step S510)

In the present flow, a defect coordinate correction formula is already created when defects in the inspection mode A were observed. Therefore, the control unit 125 corrects the defect coordinates (coordinate information acquired by the defect inspection apparatus 107) read in S301 using the defect coordinate correction formula calculated in S508. After that, the flow proceeds to S503. According to such a configuration, defects in the inspection mode B can be searched for using the defect coordinate correction formula created when the defects in the inspection mode A were observed. Therefore, the detection accuracy in the inspection mode B is improved.

Next, the order of observing defects in the aforementioned flow will be described. A defect that is initially detected with the optical microscope unit 105 is preferably a defect that is farthest from the center among the defects to be observed. The center is the center of the wafer or the center of the defects to be observed. This is in order to take into consideration a point that an error in the defect inspection apparatus 107 is large in the center or the wafer, and a point that a defect that is far from the center should be selected to increase the detection accuracy of errors.

A defect that is detected next is preferably a defect that is farthest from the initially detected defect. Alternatively, the entire wafer surface may be split into M pieces in accordance with the number of samplings, and a defect that is far from the center of each split region may be selected. In such a case, a defect that is initially detected with the optical microscope is the selected defect that is farthest from the center of the wafer among the split regions including defects and has a small azimuth θ. A defect that is detected next is the selected defect that is farthest from the center of the wafer excluding the region including the first defect, and has a small azimuth θ among the split regions including defects. Detecting defects in such an order can improve the accuracy of the defect coordinate correction formula.

The reviewing device 100 in this embodiment includes the optical microscope unit 105 and the SEM 106 (electron microscope unit). The optical microscope unit 105 includes illumination optics 201 and 211 that each irradiate the sample 101 with a laser beam, and detection optics 210 that acquire an image on the basis of reflected light or scattered light from the sample 101. The control unit 125 calculates the coordinates of a defect on the basis of the image acquired with the detection optics 210. In addition, the control unit 125 observes the defect using the SEM 106 on the basis of the calculated defect coordinates. In such a configuration, the control unit 125 sets the imaging conditions of the illumination optics (e.g., illumination spot size of the laser) of the optical microscope unit 105 for each defect on the basis of the defect information acquired by the external defect apparatus 107, and changes the imaging conditions of the optical microscope unit 105 for each defect.

According to this embodiment, before defects that can be imaged in the high-sensitivity mode (inspection mode B) are imaged, defects that can be imaged in the wide-field mode (inspection mode A) are detected, and a defect coordinate correction formula is calculated. As a defect coordinate correction formula is created in advance by detection of defects in the wide-field mode, it is possible to reduce failures in the detection of defects in the high-sensitivity mode with a narrow field of view for which higher coordinate accuracy than that in the wide-field mode is required. In addition, it is also possible to reduce the frequency of the search-around operation performed due to failures in the detection of defects in the high-sensitivity mode. Accordingly, a decrease in throughput can be suppressed.

According to this embodiment, in the reviewing device 100 having the SEM 106 and the optical microscope unit 105 mounted thereon, imaging conditions that are suitable for detecting a defect are set for each defect, and a correction formula for correcting the positional information on the defect is created, whereby high-sensitivity detection of defects becomes possible and failures in the detection of defects can be prevented. Coordinate accuracy that is necessary for detection of defects is ensured, and both high sensitivity and high throughput can be achieved. With the configuration in this embodiment, it is possible to observe defects and the like that have been generated on a semiconductor wafer during a production process of a semiconductor device, at high speed and high detection rate.

The aforementioned flow shows an example in which all of defects are observed with the SEM 106 after all of the defects are observed with the optical microscope unit 105 and a coordinate correction formula is created and updated, though the present invention is not limited thereto. For example, it is also possible to consecutively perform observation with the optical microscope unit 105 and observation with the SEM for a single defect. In the case of such an example, a single defect (first defect) is observed with the optical microscope unit 105 and the coordinate information on the first defect is corrected, and immediately after that, the first defect is observed with the SEM. After that, the second defect that is different from the first defect is observed with the optical microscope unit 105 and the coordinate information on the second defect is corrected, and then, the second defect is observed with the SEM.

In the aforementioned flow, an inspection mode is initially set for each defect when inspection is started, and the inspection mode is changed only when detection fails, though the present invention is not limited thereto. For example, when failures in the detection of defects frequently occur in the initially set inspection mode, an initial inspection mode for the following defects can be changed before the defects are searched for.

In the case of the configuration in which an inspection mode is set for each defect as shown in FIG. 4, the lens configuration of the dark-field illumination optics 201 should be changed when the inspection mode is changed. Therefore, the lens driving time and stabilization time are required each time the lens is replaced. In order to suppress the number of times of replacement of lenses to a minimum and thus reduce the total inspection time, the control unit 125 may also set the order of defects to be observed in advance on the basis of the defect information stored in the storage device 124. Further, the control unit 125 may also set the order of defects to be observed such that the moving distance of the stage 103 becomes minimum on the basis of the defect information stored in the storage device 124.

In the aforementioned flow, if a search for defects fails in the first search-around operation, the control unit 125 should determine whether to execute the second search-around operation or not (S511). In this regard, the total number of times of search around operation to be executed on a single defect may be set in advance, or may be specified by a user. As another example, the control unit 125 may calculate the total number of times of search around operation to be executed on a single defect from the total time that is tolerable to observe a single wafer in detail.

Embodiment 2

Next, Embodiment 2 will be described. As the configuration of the reviewing device in this embodiment is the same as that in FIGS. 1 to 3, the description thereof is omitted herein. This embodiment is characterized in that when an image acquired with the optical microscope unit 105 contains a plurality of defects, an ID of each defect in the image can be identified.

Figure 6:
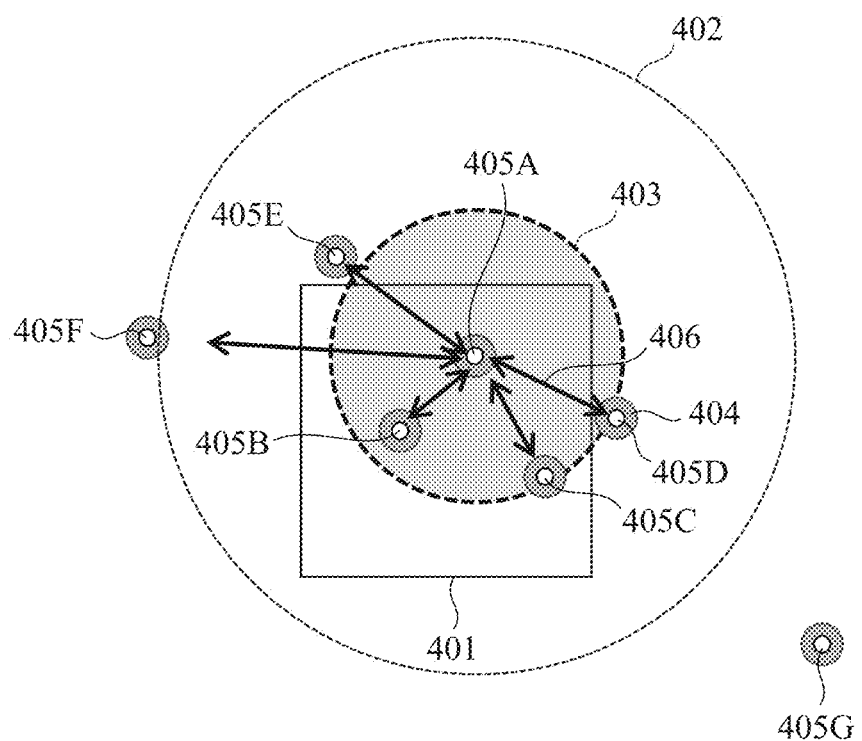
FIG. 6 is an illustration view when the field of view contains a plurality of defects.

A case where the field of view contains a plurality of defects will be described with reference to FIG. 6. Defect coordinates included in the defect information of the defect inspection apparatus 107 include a detection error 404 of the defect inspection apparatus 107 and link coordinate accuracy 403 between the defect inspection apparatus 107 and the reviewing device 100. A region 401 imaged by the optical microscope unit 105 is a narrow region of about several 100 μm. For example, in the case of the wide-field mode, the field of view has a size of 200 μm×200 μm, while in the case of the high-sensitivity mode, the field of view has a size of 100 μm×100 μm. The relative positional relationship between defects that are so close to each other that they are almost contained in the imaged region 401 is about a degree in which the relative positional relationship can be influenced by the detection error 404 of the defect inspection apparatus 107, and thus, the accuracy of the relative positional relationship is high. Herein, the relative positional relationship between defects is the distance between and/or the direction of the defects, and the like. Although FIG. 6 illustrates an example in which the positional relationship, such as the distance between and/or the direction of defects, is used as the relative relationship between the defects, it is also possible to use the relative relationship between the feature quantities of defects, such as the luminance difference between defect images or the area ratio of bright spots, as the relative relationship.

When an image of a defect 405A to be observed is captured with the optical microscope unit 105 on the basis of the defect information of the defect inspection apparatus 107, a region that may be included in the field of view is a region 402 for which the link coordinate accuracy 403 and the stage positioning accuracy are taken into consideration.

The control unit 125 extracts from the defect information of the defect inspection apparatus 107 candidate defects in the region 402 that may be included in the imaged region 401. In the case of FIG. 6, defects 405A, 405B, 405C, 405D, 405E, and 405F included in the region 402 are the candidate defects that may be included in the imaging range of the optical microscope unit 105 when the defect 405A is imaged. The defect 405E is a defect that can be included in the imaging range of the optical microscope unit 105 as it is within the region 402 if the detection error 404 of the defect inspection apparatus 107 is included.

Next, the control unit 125 derives the relative positional relationship 406 between the extracted defects 405A, 405B, 405C, 405D, 405E, and 405F. In the example of FIG. 6, the relative positional relationship includes the distance between the defects and the direction between the defects. In this case, the control unit 125 may determine the relative positional relationship between the defect 405A to be observed and other defects or determine the relative positional relationship between the defects not including the defect 405A. In addition, a pair of defects for which the relative positional relationship is to be derived may be limited to a pair of defects that can be contained in the same field of view of the optical microscope unit 105. For example, the distance between the defect 405F and the defect 405D is longer than the diagonal line of the field of view (imaged region 401) of the optical microscope unit 105 and thus is obviously not contained in the same field of view. Thus, the control unit 125 need not derive the relative positional relationship between such defects.

The control unit 125 captures an image of the defect 405A to be observed using the optical microscope unit 105. At this time, if the captured image contains only a single defect image, the control unit 125 identifies the defect image in the image as the defect 405A and calculates the coordinates thereof. Meanwhile, if the image captured with the optical microscope unit 105 contains a plurality of defects, the control unit 125 derives the relative positional relationship between the defects in the image.

Next, the control unit 125 compares the relative positional relationship between the defects derived from the defect information output from the defect inspection apparatus 107 with the relative positional relationship between the defect images in the image captured with the optical microscope unit 105, and identifies a defect ID corresponding to each of the plurality of defect images contained in the captured image. The control unit 125 stores into the storage device 124 a set of the identified defect ID and the defect coordinates obtained from the defect image.

It should be noted that when the number of defects detected from the image captured with the optical microscope unit 105 is greater than or equal to three, the control unit 125 may derive the relative positional relationship of all combinations of the imaged defects, or extract defects for which the relative positional relationship is to be derived from the imaged defects. At this time, the control unit 125 may select at least two defects from among the plurality of imaged defects. Once a defect ID corresponding to one of the selected defects can be identified, the control unit 125 can then identify a defect ID of the other defect(s) from the derived relative positional relationship. Therefore, there is no problem even if the selected defects are those other than the defect to be observed. When the number of selected defects is small, there is an advantage in that the processing speed can be increased. Meanwhile, when a selected defect has not been detected by the defect inspection apparatus 107 and a corresponding defect ID cannot thus be identified, the control unit 125 may select other defects again.

When the image captured with the optical microscope unit 105 does not contain the defect to be observed, the control unit 125 determines a region in which the defect to be observed can be imaged from the relative positional relationship between the detected defect in the captured image obtained on the basis of the defect information of the defect inspection apparatus 107 and the defect to be observed, and moves the stage 103 so that the region is included in the field of view of the optical microscope unit 105. In the foregoing, if there is no defect that can be included in the imaging range of the optical microscope unit 105 other than the defect to be observed, the following flow need not be executed.

Figure 7:
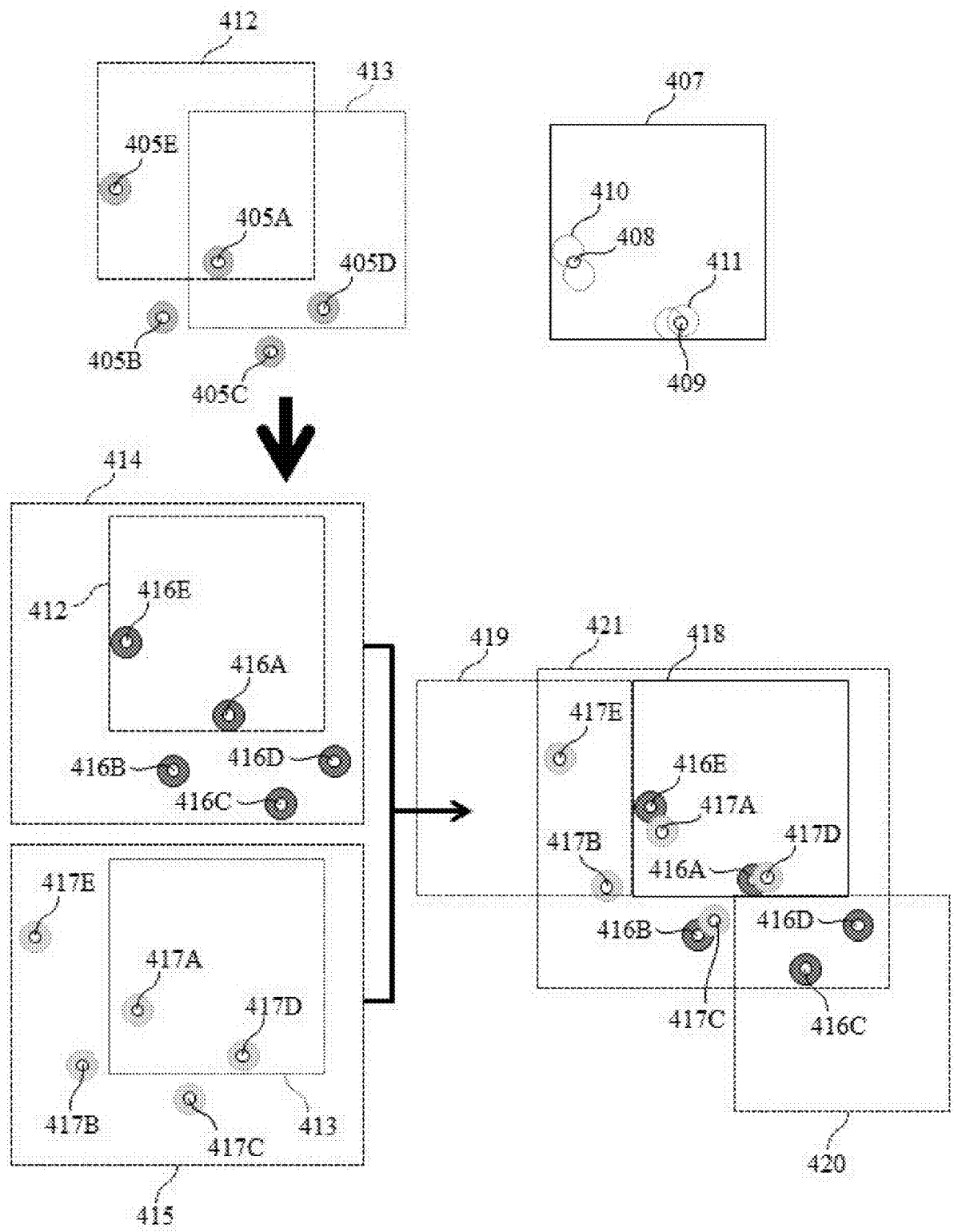
FIG. 7 is an illustration view when the field of view contains a plurality of defects and also when there is a plurality of candidate imaged defects.

Next, a case where there is a plurality of defects and there is also a plurality of candidate imaged defects will be described with reference to FIG. 7. For example, suppose that when an image of the defect 405A to be observed is captured with the optical microscope unit 105, an image indicated by a captured image 407 is obtained. Defect images detected from the captured image 407 are two as indicated by reference numerals 408 and 409. At this time, when the relative positional relationships between defects around the detect 405A to be observed are compared with one another as described above with reference to FIG. 6, there are two regions 412 and 413 that are the candidate imaged regions, and thus, defect IDs corresponding to the defect images 408 and 409 in the captured image 407 cannot be identified. If the captured image 407 corresponds to the region 412, a defect image corresponding to the defect 405A is the defect image 409, while if the captured image 407 corresponds to the region 413, a defect image corresponding to the defect 405A is the defect image 408. It should be noted that the regions 410 and 411 each indicate the range of the coordinate accuracy of the defect inspection apparatus 107.

If the captured image 407 corresponds to the region 412, the arrangement relationship of defects 416A to 416E as shown in a region 414 around the imaged region should be obtained. Meanwhile, if the captured image 407 corresponds to the region 413, the arrangement relationship of defects 417A to 417E as shown in a region 415 around the imaged region should be obtained.

When the regions 412 and 413 are laid one on top of the other, inclusive of the defects 416A to 416E and 417A to 417E around the imaged region, an image 421 is obtained. A region 418 is the imaged region. The control unit 125 extracts from the image 421 a region having a great difference between the candidate defect arrangements 416 and 417 around the imaged region around the region 418. It is acceptable as long as a region extracted herein is a region in which a difference between the candidate defects is generated. Preferably, a region having the greatest difference between the candidate defects is extracted around the imaged region. The control unit 125 captures an image of the region with the greatest difference using the optical microscope unit 105, and identifies a defect ID corresponding to each defect image in the captured image 407 on the basis of the captured image.

For example, in the case of the image 421, a region 419 and a region 420 are regions each having a great difference. For example, the control unit 125 captures an image of the region 419 on the left side of the imaged region using the optical microscope unit 105. If the image contains a defect, the control unit 125 can identify that the captured image 407 corresponds to the region 413. Meanwhile, if the image does not contain any defect, the control unit 125 can identify that the captured image 407 corresponds to the region 412.

Figure 8:
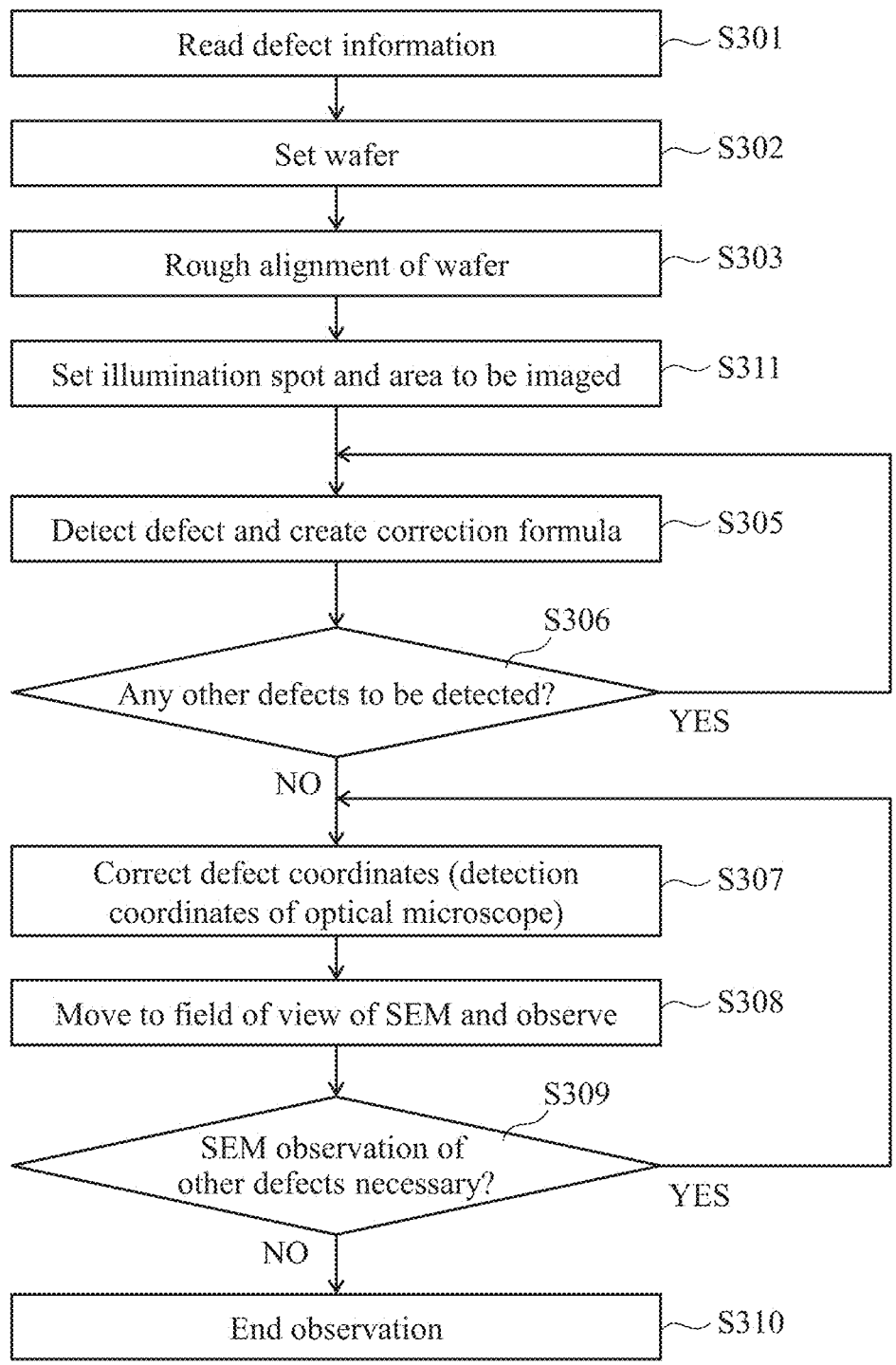
FIG. 8 is a flowchart showing a flow of a defect observation process in Embodiment 2 of the present invention.
Figure 9:
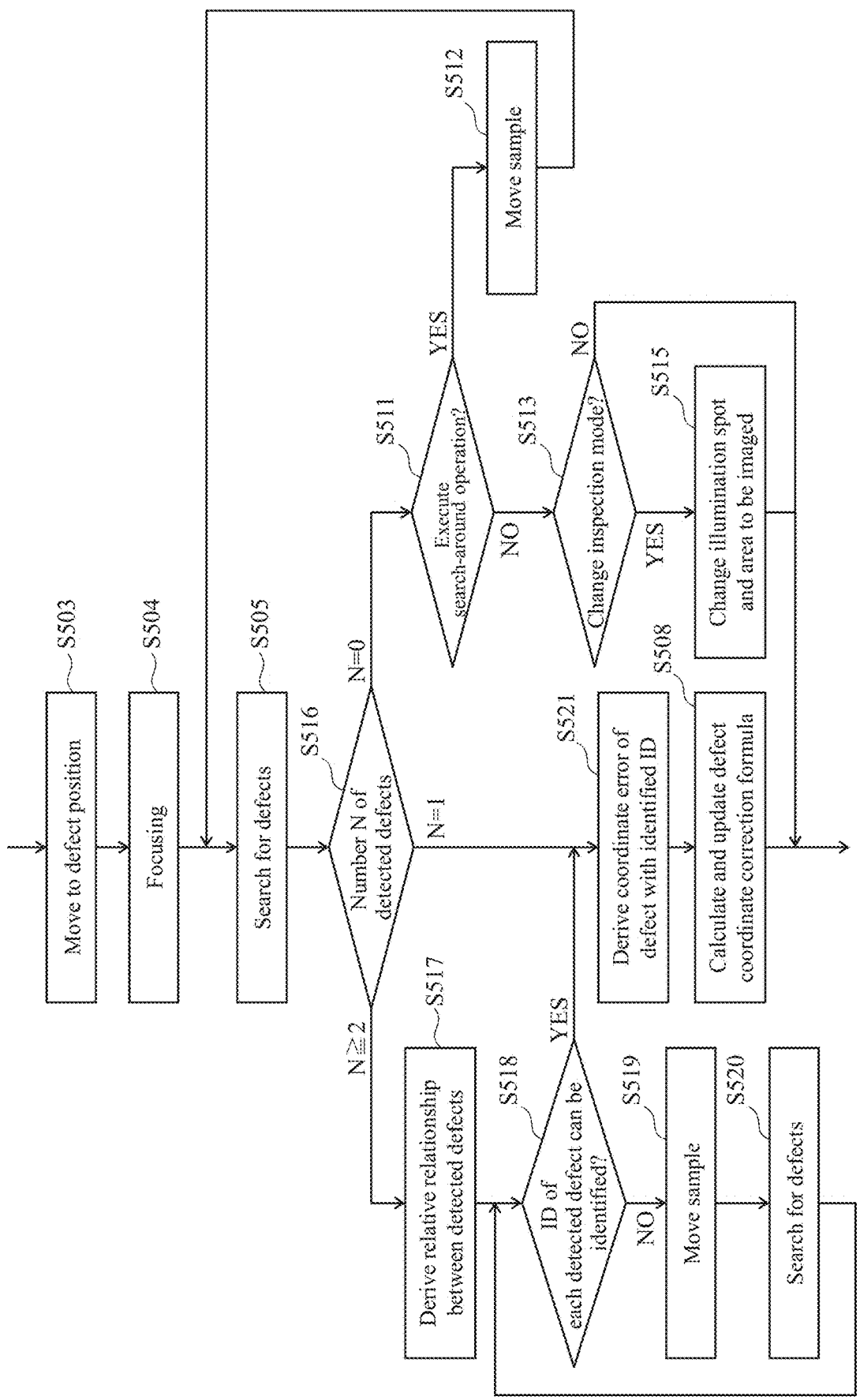
FIG. 9 is a flowchart showing a detailed flow of a defect detection and correction formula creation step in FIG. 8.

FIG. 8 is a flowchart showing a flow of the defect observation process in this embodiment. FIG. 9 is a flowchart showing a detailed flow of the defect detection and correction formula creation step in FIG. 8. Regarding the steps whose reference numerals are the same as those in FIGS. 4 and 5, the detailed description will be omitted. Although FIG. 8 shows an example in which an inspection mode is specified when inspection is started and inspection is performed in the same mode until the end unless detection of defects fails, the present invention is not limited thereto. As shown in the flow of FIG. 4, it is also possible to specify an inspection mode in advance for each defect to be observed and change the inspection conditions for each defect.

(Step S311)

The control unit 125 changes the lens configuration and arrangement of the dark-field illumination optics 201 in accordance with an inspection mode set in advance, thereby setting an illumination spot. Along with this, the control unit 125 sets an area to be imaged to limit the pixels to be used by the detector 207 when cutting out the pixels of the detector 207. In addition, the control unit 125 also sets parameters that are necessary for imaging, such as the illumination laser power, polarization, and detection time.

(Step S516)

The control unit 125 determines the number of defects N detected from the image of the optical microscope unit 105 acquired in S505. If the number N of the detected defects is greater than or equal to 2, the flow proceeds to S517. If the number N of the detected defects is 1, the flow proceeds to S521. In addition, if the number N of the detected defects is zero, the flow proceeds to S511.

(Step S517)

If the number N of the detected defects is greater than or equal to 2, the control unit 125 derives the relative relationship between defect images in the image acquired in S505. The relative relationship herein includes one or more of the distance between and direction of the defect images, luminance difference, or the area ratio of bright spots. If the number N of the detected defects is greater than or equal to 3, the control unit 125 may derive the relative relationship between all of the defects, or extract at least two defects and derive the relative relationship therebetween. Using the relative positional relationship between all of the defects can improve the accuracy of the identification of defect IDs. Meanwhile, extracting some of the defects can reduce the processing time required for identifying defect IDs.

(Step S518)

The control unit 125 compares the relative relationship between the defects derived in S517 with the relative relationship between the candidate defects calculated from the defect information of the defect inspection apparatus 107, and determines whether a defect ID corresponding to each defect image in the image acquired in S505 can be identified or not. If it is determined that the defect ID can be identified (YES), the flow proceeds to S521. If it is determined that the defect ID cannot be identified (NO), the flow proceeds to S519.

If there is a defect whose defect ID cannot be identified, the control unit 125 may determine that the defect has not been detected by the defect inspection apparatus 107. In such a case, the control unit 125 may assign a new ID to the defect. In addition, the control unit 125 may provide the defect with information that explicitly indicates that the defect has not been detected by the defect inspection apparatus 107.

(Step S521)

If it is determined that the defect ID can be identified in S518, and if the number N of the detected defects is determined to be 1 in S516, the control unit 125 calculates error data between the coordinate information on the defect image with the ID calculated with the optical microscope unit 105 and the coordinate information on the defect with the ID output from the defect inspection apparatus 107. For example, the error calculated herein is an error of the position of the center of gravity of the defect image. The error data calculated in S521 is used to calculate the defect coordinate correction formula in S508 as in Embodiment 1.

If it is determined in S518 that there is a plurality of defects whose defect ID has been identified, the control unit 125 similarly calculates error data for all of the plurality of defects. The error data is derived not only for the defect to be observed but also for the defects whose defect IDs have been identified.

(Step S519)

If defect IDs cannot be identified in S518, the control unit 125 selects a region in which defect IDs of the defect images in the region imaged in S504 can be identified on the basis of the defect information of the defect inspection apparatus 107, and moves the stage 103 so that the selected region is included in the field of view of the optical microscope unit 105. For example, the control unit 125 extracts a region having a great difference between candidate defect arrangements around the imaged region as described with reference to FIG. 7. Then, the control unit 125 moves the stage 103 so that the region with the great difference is included in the field of view of the optical microscope unit 105.

(Step S520)

The control unit 125 captures an image of the region selected in S519 using the optical microscope unit 105, and searches the captured image for defects. If the search for defects fails in the second imaging process, it is necessary to determine whether to execute the third imaging process or not. At this time, the upper limit of the number of imaging processes to be performed to identify defect IDs may be specified by a user, or be calculated from the total time that is tolerable to observe a single wafer in detail.

Although FIG. 9 illustrates an example in which, if defect IDs cannot be identified in S518, a region having a great difference between candidate defect arrangements around the imaged region is extracted and the extracted region is imaged, the present invention is not limited thereto. For example, if defect IDs cannot be identified in S518, there is a possibility that minute defects may be buried due to the influence of a huge defect image, for example. Thus, in such a case, the control unit 125 may select defects for which the relative relationship is to be derived again, and execute the steps of S517 to S518 again.

Meanwhile, if the defect ID of the defect to be observed cannot be identified, the control unit 125 may select a region in which the defect to be observed is predicted to be imageable from the relative relationship with the defect ID identified in S518, and capture an image of the region using the optical microscope unit 105 again. In addition, if the region that can be imaged does not contain the defect to be observed, the control unit 125 may determine that the information from the defect inspection apparatus 107 is false and thus abandon the observation of defects.

If the number N of the detected defects is determined to be zero in S516, processes similar to those in S511 to S513 in FIG. 5 are performed. If it is determined that the inspection mode should be changed in S513, the flow proceeds to S515.

(Step S515)

The control unit 125 changes the initial inspection mode selected in S311 to another inspection mode. The control unit 125 changes the lens configuration and arrangement of the dark-field illumination optics 201 to change the illumination spot. Along with this, the control unit 125 changes the area to be imaged to limit the pixels to be used by the detector 207 when cutting out the pixels of the detector 207. In addition, the control unit 125 may also change parameters that are necessary for imaging, such as the illumination laser power, polarization, and detection time.

According to this embodiment, even when an image acquired with the optical microscope unit 105 contains a plurality of defects, the defect to be imaged can be identified from a plurality of defect images in the acquired image. Therefore, the target defect can be accurately observed with the SEM. In addition, as the risk of erroneously determining a non-target defect as the target defect can be reduced, a decrease in the accuracy of the defect coordinate correction formula can be prevented. Therefore, the frequency of search-around operation performed due to failures in the detection of defects can be reduced, and a decrease in throughput can thus be suppressed.

Although this embodiment has described a method of comparing the relative relationships between defects with one another as a means for identifying the region imaged by the optical microscope unit 105, the present invention is not limited thereto.

For example, the control unit 125 may create a pseudo image of candidate defects in the region 402 that can be imaged by the optical microscope unit 105, and execute template matching between the created pseudo image and the image captured with the optical microscope unit 105. Examples of the template matching method include normalized correlation. In this case, the control unit 125 may create a pseudo image by blurring defect images taking into consideration coordinate errors. For example, a method of convoluting a Gaussian function or the like is considered as a method of creating a blurred pseudo image.

Figure 10:
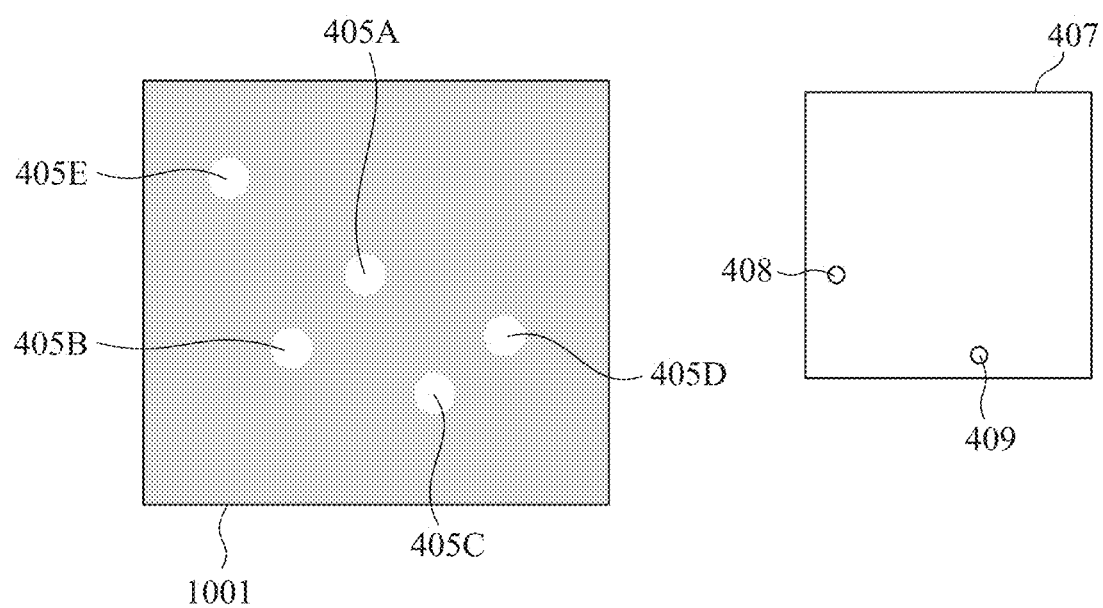
FIG. 10 is a view illustrating identification of a defect ID through template matching.

FIG. 10 illustrates an example of template matching. The control unit 125 creates a pseudo image 1001 that is a blurred image of the defect images of the defects 405A, 405B, 405C, 405D, 405E, and 405F from the defect information of the defect information device 107. The control unit 125 executes template matching with the captured image 407 on the pseudo image 1001. The control unit 125 may search for a position at which the evaluation value of the template matching is the highest, and identify the corresponding defect ID from the relationship with the position.

Embodiment 3

Next, Embodiment 3 will be described. As the configuration of the reviewing device in this embodiment is the same as that in FIGS. 1 to 3, the description thereof is omitted herein. This embodiment is characterized in that when it is determined that an image captured with the optical microscope unit 105 may contain a plurality of defects and there may also be a great difference in luminance between the defects, defect coordinates can be derived from the image of the optical microscope unit 105.

Figure 11:
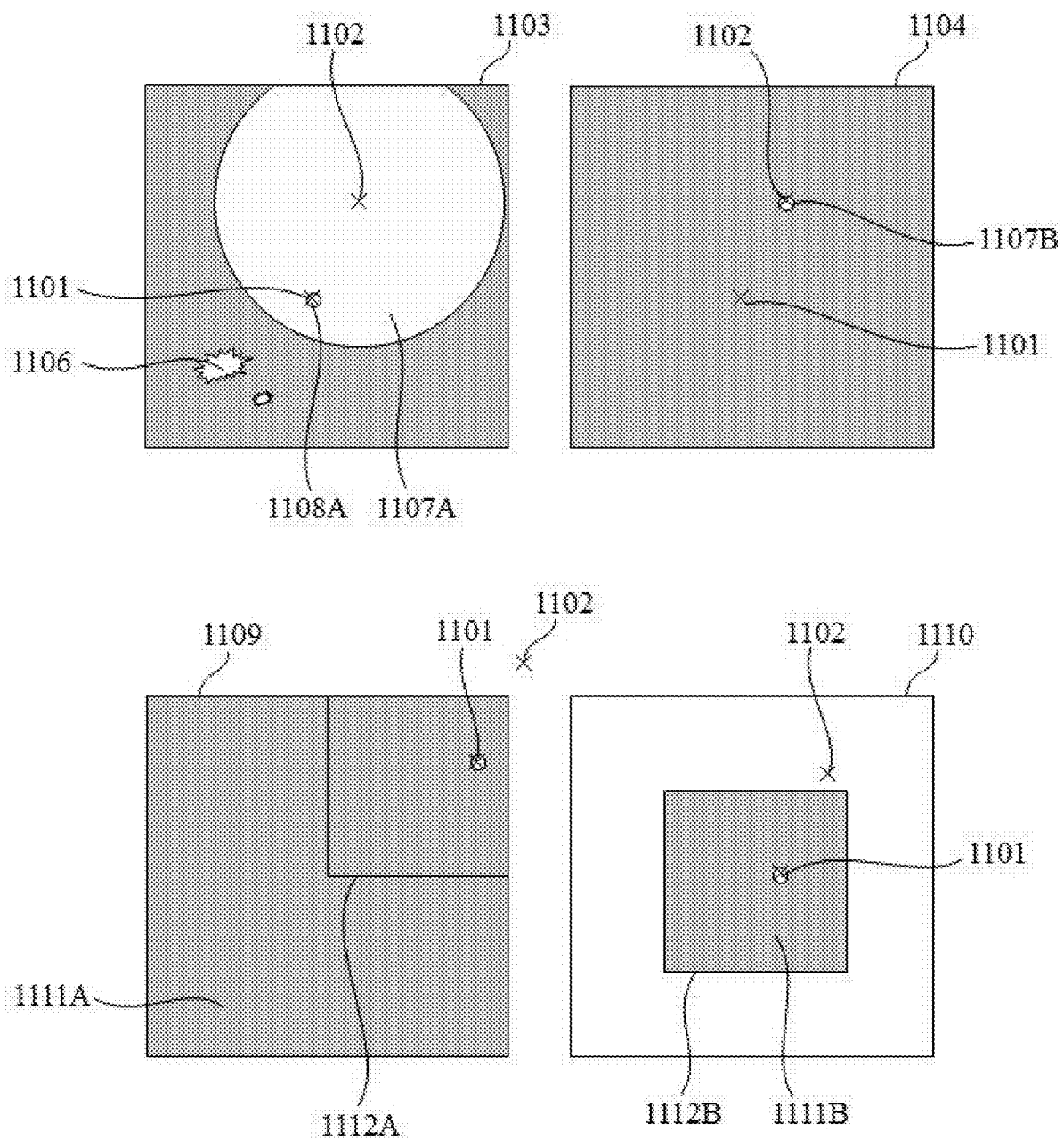
FIG. 11 is an illustration view when the field of view contains a plurality of defects and also when there is a great difference in luminance between the defects.

A case where the field of view contains a plurality of defects and the difference in luminance between the defects is greater than a predetermined value will be described with reference to FIG. 11.

Suppose that when there is a great difference in size between defects that are close to each other, the inspection mode and imaging conditions are adjusted to those for a defect 1101 with a smaller size (hereinafter referred to as a smaller defect). In such a case, as shown in an image 1103, the smaller defect 1101 may be buried in a defect image 1107A of a defect 1102 with a larger size (hereinafter referred to as a larger defect) or in stray light 1106 (ghost) derived from scattered light from the larger defect 1102, so that a defect image 1108A of the smaller defect 1101 becomes difficult to detect. Further, the defect image 1107A of the larger defect 1102 may include not only a defect image but also smear and blooming.

Meanwhile, if the inspection mode and imaging conditions are adjusted to those for the large defect 1102, the larger defect 1102 can be detected as shown in an image 1104 (defect image 1107B). The smaller defect 1101 cannot be detected as it has low luminance.

It should be noted that the defect size described herein means not a physical size but a size that is estimated from the amount of scattered light and luminance when imaging is performed with the optical microscope. In the following example, a luminance difference is used to estimate the difference in size between defects. It is also possible to use information on the defect size that is contained in the defect information of the defect information device 107.

In this embodiment, when the luminance difference between defects that are close to each other is greater than a predetermined value, a larger defect and a smaller defect that are close to each other are handled as a set. When an image captured with the optical microscope unit 105 contains a plurality of defects and the luminance difference between the plurality of defects is greater than a predetermined value, the control unit 125 sets the imaging conditions for a defect with the highest luminance value among the plurality of defects, and thereafter sets the imaging conditions for the other defects among the plurality of defects.

For example, the control unit 125 first acquires an image in the inspection mode and under the imaging conditions that are suitable for detecting a larger defect, and detects the larger defect from the acquired image, and then derives the coordinates of the larger defect. At this time, the imaging coordinates are selected so that the field of view contains the larger defect.

Next, the control unit 125 acquires an image in the inspection mode and under the imaging conditions that are suitable for detecting a smaller defect, and detects the smaller defect from the acquired image, and then derives the coordinates of the smaller defect. The region imaged herein is determined on the basis of the defect information of the defect information device 107 and the previously derived coordinates of the larger defect.

The accuracy of the relative positional relationship between the defects, which are close to each other, obtained on the basis of the defect information of the defect inspection apparatus 107 is at the level of the detection accuracy of the defect inspection apparatus 107, that is, high accuracy as the distance between the defects is close. Thus, as shown in an image 1109, the control unit 125 may, when capturing an image of the smaller defect 1101, move the larger defect 1102 to a region where the illumination intensity is low, and also move the stage 103 so that the smaller defect 1101 is in the detectable region. At this time, the control unit 125 may also cut out a region 1112A around the smaller defect 1101.

In addition, as shown in an image 1110, the control unit 125 may reduce the illumination spot size (region 1111B) and cut out a region 1112B around the smaller defect 1101. Reducing the spot size can suppress the amount of scattered light from the larger defect 1102. At this time, the control unit 125 may also move the stage 103 so that the larger defect 1102 is outside a region where the illumination intensity is high and the smaller defect 1101 is in the imageable region. In addition, it is also possible to only reduce the illumination spot size and select the region to be cut out without shifting the stage.

Figure 12:
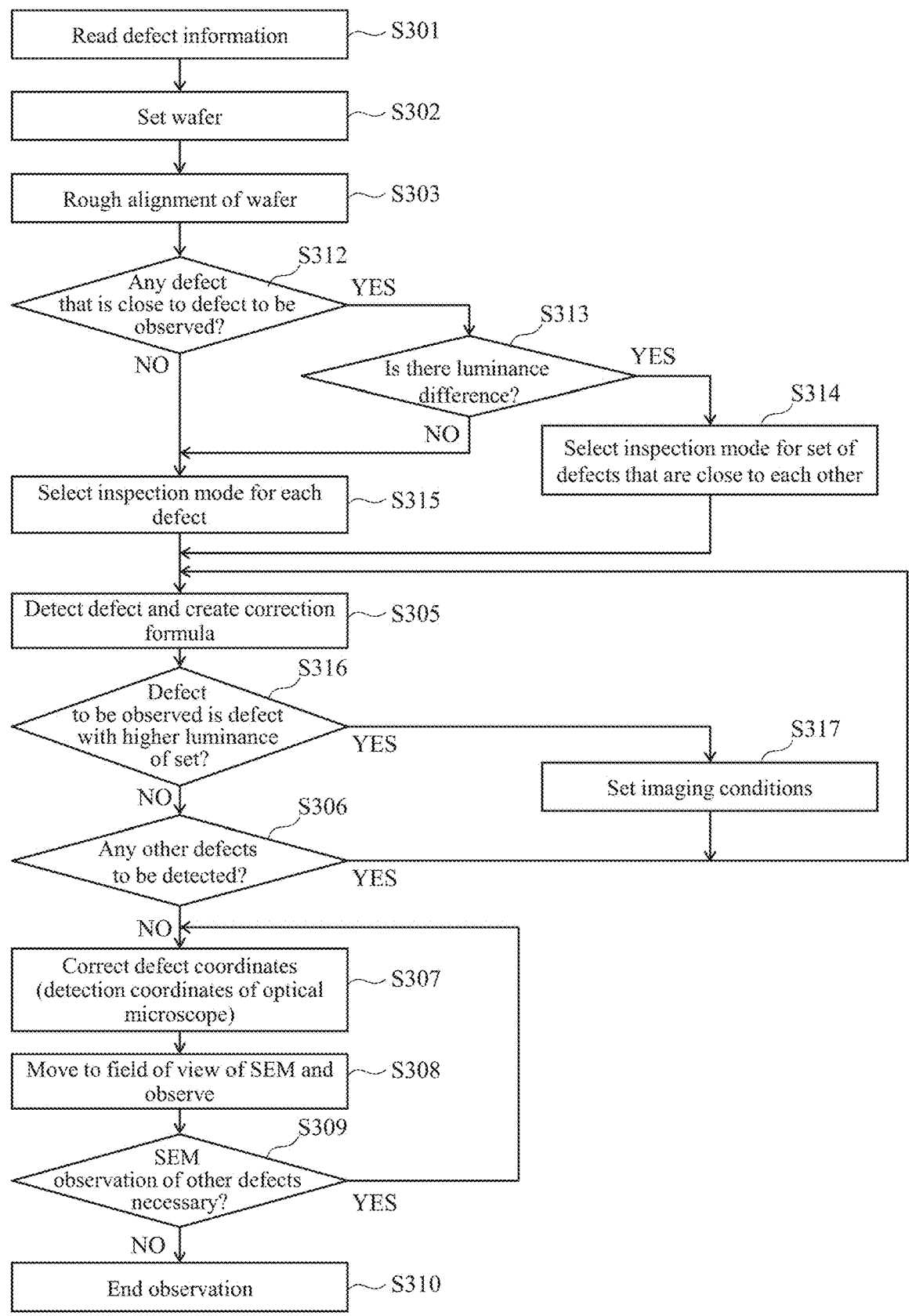
FIG. 12 is a flowchart showing a flow of a defect observation process in Embodiment 3 of the present invention.

FIG. 12 is a flowchart showing a flow of the defect observation process in this embodiment. Regarding the steps whose reference numerals are the same as those in FIG. 4, the detailed description is omitted. Although FIG. 12 shows an example in which the inspection mode is specified in advance for each defect to be observed and the inspection conditions are changed for each defect, the present invention is not limited thereto.

(Step S312)

The control unit 125 determines whether there are other defects in a region around the defect to be observed on the basis of the defect information read in S301. The "region around the defect to be observed" herein is a region that can be included in the field of view when the defect to be observed is imaged with the optical microscope unit 105. If there are other defects in the region around the defect to be observed, the flow proceeds to S313. If there are no other defects in the region around the defect to be observed, the flow proceeds to S315.

In addition, the control unit 125 may set the area around the defect to be observed in accordance with the difference in size of the defects on the basis of the difference in size between the detect to be observed obtained from the defect information read in S301 and another defect as well as the illumination intensity distribution. For example, if there is a great difference in size between the defect to be observed and another defect and it is thus predicted that there will be an influence of stray light even if the other defect is located outside the field of view, the control unit 125 may determine that there is another defect around the defect to be observed.

(Step S313)

The control unit 125, if it is determined that there is a defect that is close to the defect to be observed in S312, determines the magnitude of the luminance difference between the defects that are close to each other on the basis of the defect information read in S301. If there is a luminance difference of greater than or equal to a threshold between the defects that are close to each other (YES), the flow proceeds to S314. Meanwhile, if the luminance difference between the defects that are close to each other is less than the threshold (NO), the flow proceeds to S315.

(Step S314)

The control unit 125 sets an inspection mode by handling the defect to be observed and the defect that is close thereto as a set. Examples of the inspection mode include the inspection mode A in which inspection is performed with a wider illumination spot to suppress failures in the detection of defects and the inspection mode B in which inspection is performed with a narrower illumination spot to defect defects with high sensitivity. The control unit 125 selects the inspection mode A with a wide field of view for a defect with a larger size (larger defect) of the set, and selects the inspection mode B with a narrow field of view for a defect with a smaller size (smaller defect) of the set. Accordingly, in the following steps, it becomes possible to acquire an image in the inspection mode and under the imaging conditions that are suitable for detecting a larger defect, and thus correct the coordinates of the larger defect. Further, it also becomes possible to acquire an image in the inspection mode and under the imaging conditions that are suitable for detecting a smaller defect, and thus correct the coordinates of the smaller defect.

(Step S315)

If it is determined that there are no other defects around the defect to be observed in S312 and the luminance difference between the defects that are close to each other is determined to be less than a threshold in S313, the control unit 215 selects an initial inspection mode for each defect on the basis of the defect information read in S301.

(Step S305)

The process in S305 is similar to that in FIG. 5. As shown in FIG. 5, in this example also, detection of defects in the inspection mode A is continuously executed until detection of all defects set in the inspection mode A is completed. After that, inspection of defects in the inspection mode B is executed. Upon termination of step S305, the flow proceeds to S316.

It should be noted that the process in S305 is not limited to that shown in FIG. 5. For example, detection of defects may be executed with the inspection mode switched for each defect.

(Step S316)

The control unit 125 determines whether the defect to be observed is a defect with higher luminance of the set that has been set in S314. If the defect to be observed is determined to be a defect with higher luminance, the flow proceeds to S317. If the defect to be observed is determined to be a defect with lower luminance, the flow proceeds to S306.

(Step S317)

The control unit 125 sets the imaging conditions (inspection mode B) to capture an image of the defect with lower luminance of the set that has been set in S314. The imaging conditions set herein may include the illumination spot size, the shift amount of the stage, a region of the field of view to be cut out, detection conditions, and the like. In addition, the imaging conditions may also be set on the basis of the relative relationship (luminance difference and distance between the defects) obtained from the defect information of the defect inspection apparatus 107 read in S301. After the imaging conditions for the defect with lower luminance are set, the flow returns to S305, and then, the defect detection and correction formula creating step is executed.

According to this embodiment, even when a defect having a great difference in size is located close to the detect to be observed, the defect coordinates can be derived. Conventionally, when the difference in size between defects that are close to each other is large, a defect with a smaller size cannot be detected as it is buried in a defect image of a defect with a larger size or in stray light resulting from scattered light from the defect with a larger size. According to this embodiment, it is possible to set a set of defects having a great difference in size, and set an inspection mode and imaging conditions for each defect in the set. That is, it is possible to change the inspection mode and imaging conditions on the basis of the number of defects in and the luminance information on an image acquired with the detection optics. Accordingly, even when a defect having a great difference in size is located close to the defect to be observed, it is possible to derive the defect coordinates and perform observation with the SEM.

Embodiment 4

Next, Embodiment 4 will be described. As the configuration of the reviewing device in this embodiment is similar to that in FIGS. 1 to 3, the description thereof is omitted herein. In this embodiment, an inspection mode is selected for each defect as in FIGS. 4 and 5, and defects in the wide-field mode are preferentially imaged, and also, a defect coordinate correction formula is derived, and then, defects in the high-sensitivity mode with a narrow field of view are imaged on the basis of the derived defect coordinate correction formula. In addition to such a configuration, this embodiment is characterized in that defect coordinates can be derived even when the field of view of the optical microscope unit 105 contains a plurality of defects.

Figure 13:
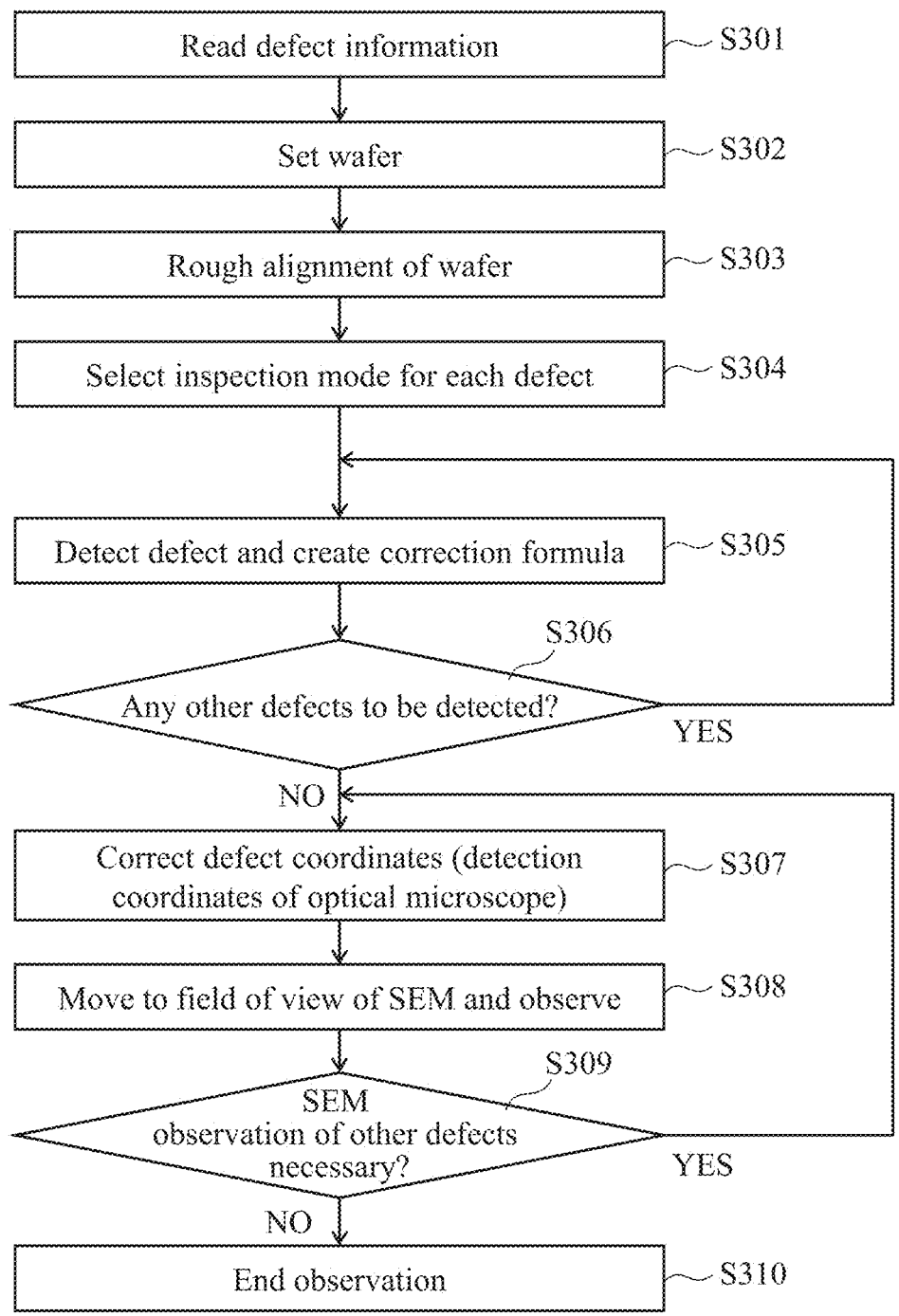
FIG. 13 is a flowchart showing a flow of a defect observation process in Embodiment 4 of the present invention.
Figure 14:
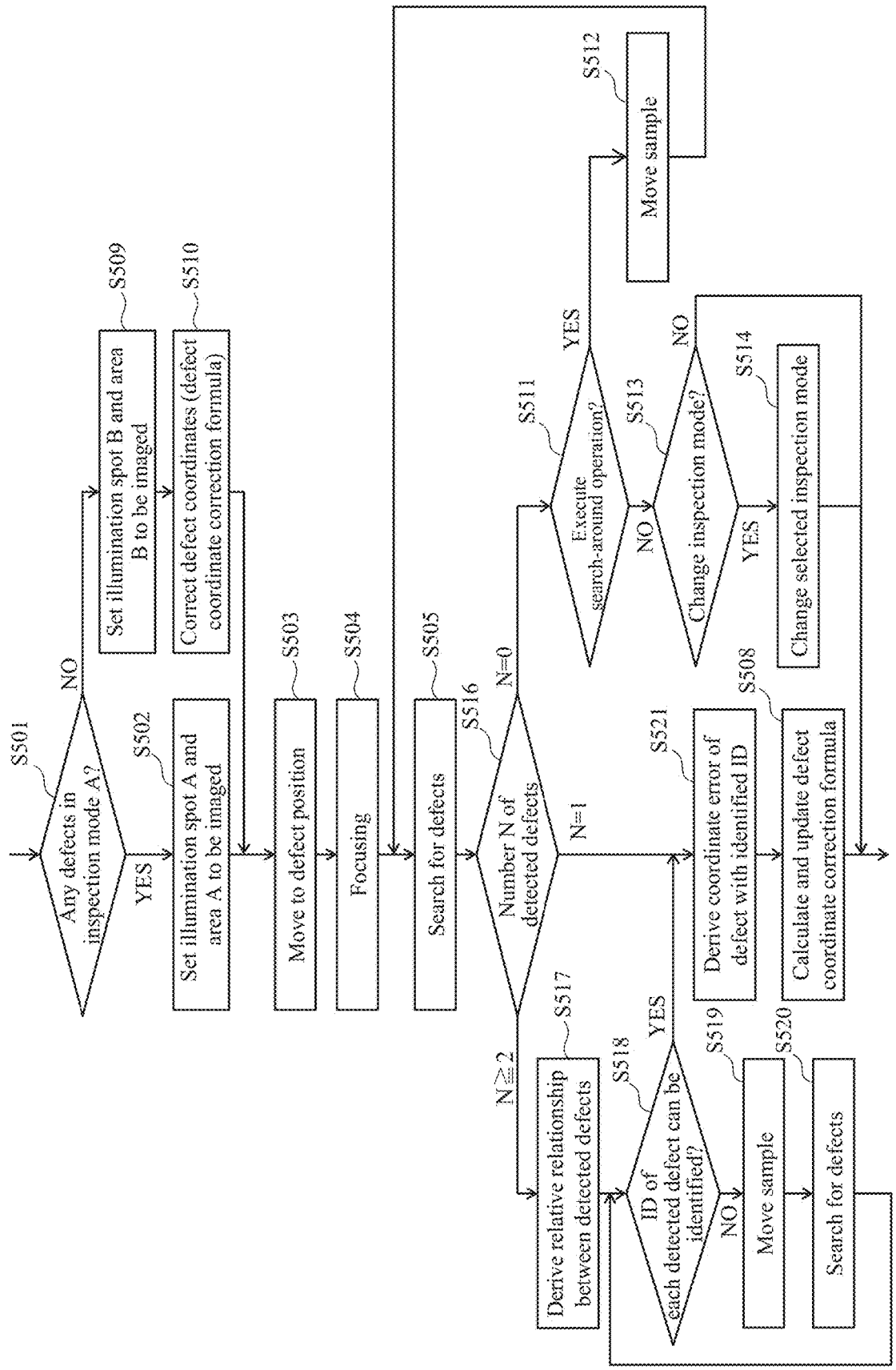
FIG. 14 is a flowchart showing a detailed flow of a defect detection and correction formula creating step in FIG. 13.

FIG. 13 is a flowchart showing a flow of the defect observation process in this embodiment. FIG. 14 is a flowchart showing a detailed flow of the defect detection and correction formula creating step S305 in FIG. 13. As the flows in FIGS. 13 and 14 are a combination of the flows in Embodiments 1 and 2, each step is indicated by the same reference numeral as that in FIGS. 13 and 14, and the detailed description thereof will thus be omitted.

It should be noted that the number N of defects detected in S516 of FIG. 14 may be the number of defects that are contained in the same field of view of the optical microscope unit 105 or the total number of defects that are detected when the search-around operation is executed at the periphery. If the number N of the detected defects is the total number of defects that are detected in the search-around operation, such defects need not be contained in the same field of view.

It should be noted that the present invention is not limited to the aforementioned embodiments, and includes a variety of variations. For example, although the aforementioned embodiments have been described in detail to clearly illustrate the present invention, the present invention need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add, remove, or substitute a configuration of another embodiment.

The aforementioned configurations, functions, and the like may be implemented by software through analysis and execution of a program that implements each function by a processor. Information such as the program that implements each function and files can be stored in a recording device such as memory, a hard disk, or a SSD (Solid State Drive); or a recording medium such as an IC card, an SD card, or a DVD. Some or all of the aforementioned configurations and the like may be implemented as hardware by designing an integrated circuit(s), for example.

In the aforementioned embodiments, the control lines and information lines represent those that are considered to be necessary for the description, and do not necessarily represent all of the control lines and information lines that are necessary for a product. Thus, in practice, almost all structures may be considered to be mutually connected.

DESCRIPTION OF SYMBOLS

100 Reviewing device
101 Sample

102 Sample holder
103 Stage
104 Optical height detector
105 Optical microscope unit
106 Electron microscope unit
107 Defect inspection apparatus
121 Network
122 Database
123 User interface
124 Storage device
125 Control unit
151 Electron beam source
152 Extracting electrode
153 Deflecting electrode
154 Objective lens electrode
155 Secondary electron detector
156 Reflected electron detector
201 Dark-field illumination optics
210 Detection optics
211 Bright-field illumination optics
1000 Defect observation apparatus

What is claimed is:

1. A defect observation apparatus, comprising:
a storage device configured to store defect information about a plurality of defects detected by an external inspection apparatus;
a first imaging unit configured to capture an image of a defect among the plurality of defects using a first imaging condition and a second imaging condition, the first imaging condition being related to wide field-of-view imaging and the second imaging condition being related to narrow field-of-view imaging;
a control unit comprising a processor configured to correct positional information on the defect using the image captured with the first imaging unit; and
a second imaging unit configured to capture an image of the defect on the basis of the corrected positional information,
wherein:
the control unit processor is configured to
set one of the first imaging condition or the second imaging condition for each of the plurality of defects,
capture an image of a first-defect that is set to the first imaging condition, using the first imaging unit,
create a correction formula on the basis of a distance and a direction of the defect information on the first-defect and relative distance and direction positional information on the first-defect detected with the first imaging unit,
correct positional information on a second-defect that is set to the second imaging condition, using the correction formula,
capture an image of the second-defect using the first imaging unit on the basis of the corrected positional information on the second-defect, and
when the image captured with the first imaging unit contains a plurality of defects,
extract, from the defect information, a plurality of candidate defects that are possibly contained in the captured image,
capture a plurality of images, using said first imaging unit under said second imaging condition, each of said plurality of images being a different field of view and containing a different set of said candidate defects, and
positively identify a defect ID of each of said first-defect from among a plurality of candidate defects in the plurality of captured images on the basis of a relative relationship between each of one or more of said candidate defects and a relative coordinate relationship between corresponding ones of said plurality of defects contained in each captured image based on said positional information of said first-defect.

2. The defect observation apparatus according to claim 1, wherein:
when the first-defect that is set to the first imaging condition includes a plurality of first-defects, the control unit processor is configured to continuously capture images of the plurality of first-defects using the first imaging unit, and capture an image of the second-defect using the first imaging unit after completion of imaging of the plurality of first-defects.

3. The defect observation apparatus according to claim 2, wherein:
the control unit processor is configured to, using the correction formula created with regard to a firstly captured defect among the plurality of first-defects, correct positional information on second and following defects among the plurality of first-defects.

4. The defect observation apparatus according to claim 1, wherein:
the control unit processor is configured to change the imaging condition for the first-defect to the second imaging condition when the image captured with the first imaging unit does not contain the first-defect.

5. The defect observation apparatus according to claim 1, wherein
the control unit processor is configured to, when the defect ID is not identified in the captured image:
overlay a plurality of candidate imaged regions to obtain a region which is larger than and which surrounds each of the plurality of candidate imaged regions;
capture one of said plurality of candidate imaged regions having largest difference in distance and direction between each of a plurality of candidate defects in which said region which is larger than and which surrounds each of the plurality of candidate imaged regions captured with the first imaging unit; and
identify the defect ID of each defect in said captured candidate image region on the basis of the defect image of the captured candidate imaged region.

6. The defect observation apparatus according to claim 1, wherein:
the control unit processor is configured to, when the defect ID is not identified in the captured image,
create a pseudo image of the candidate defects, and
identify the defect ID of each defect in the captured image through template matching between the pseudo image and the captured image.

7. The defect observation apparatus according to claim 1, wherein:
the control unit processor is configured to, when the image captured with the first imaging unit contains a plurality of defects and a luminance difference between the plurality of defects is greater than a predetermined value,
set the first imaging condition on a defect with a higher luminance value of the plurality of defects, and set the second imaging condition on a defect with a lower luminance value of the plurality of defects.

8. A defect observation apparatus, comprising:
a storage device configured to store defect information about a plurality of defects detected by an external inspection apparatus;
a first imaging unit configured to capture an image of a defect corresponding to a specified defect ID of said defect, said defect ID being associated with positional information of said defect;
a control unit comprising a processor configured to correct positional information on the defect using the image captured with the first imaging unit; and
a second imaging unit configured to capture an image of the defect on the basis of the corrected positional information,
wherein:
the control unit processor is configured to, when the image captured with the first imaging unit contains a plurality of defects,
extract, from the defect information, a plurality of candidate defects that are possibly contained in the captured image,
capture a plurality of images, using said first imaging unit, each a said plurality of images being a different field of view and containing a different set of said candidate defects,
identify, from said plurality of captured images, a defect corresponding to the defect ID from among a plurality of candidate defects in the plurality of captured images on the basis of a relative relationship between the candidate defects and a relative relationship between the plurality of defects contained in the plurality of captured images, and
correct positional information on the defect corresponding to the defect ID.

9. The defect observation apparatus according to claim 8, wherein
the control unit processor is configured to, when the defect ID is not identified in the captured image:
overlay a plurality of candidate imaged regions to obtain a region which is larger than and which surrounds each of the plurality of candidate imaged regions;
capture one of said plurality of candidate imaged regions having largest difference in distance and direction between each of a plurality of candidate defects in which said region which is larger than and which surrounds each of the plurality of candidate imaged regions captured with the first imaging unit; and
identify the defect ID of each defect in said captured candidate image region on the basis of the defect image of the captured candidate imaged region.

10. The defect observation apparatus according to claim 8, wherein:
the control unit processor is configured to, when the defect corresponding to the defect ID is not identified in the captured image,
create a pseudo image of the candidate defects, and
identify the defect corresponding to the defect ID through template matching between the pseudo image and the captured image.

11. The defect observation apparatus according to claim 8, wherein:
the control unit processor is configured to, when the image captured with the first imaging unit contains a plurality of defects and a luminance difference between the plurality of defects is greater than a predetermined value,
set an imaging condition corresponding to a defect with the highest luminance value of the plurality of defects, and thereafter set an imaging condition corresponding to another defect of the plurality of defects.

12. The defect observation apparatus according to claim 8,
wherein:
the first imaging unit is configured to capture an image of a defect among the plurality of defects using a first imaging condition and a second imaging condition, the first imaging condition being related to wide field-of-view imaging and the second imaging condition being related to narrow field-of-view imaging, and
the control unit processor is further configured to
set one of the first imaging condition or the second imaging condition for each of the plurality of defects,
capture an image of a first-defect that is set to the first imaging condition using the first imaging unit,
create a correction formula on the basis of a distance and a direction of the defect information on the first-defect and relative distance and direction positional information on the first-defect detected with the first imaging unit,
correct positional information on a second-defect that is set to the second imaging condition using the correction formula, and
capture an image of the second-defect with the first imaging unit on the basis of the corrected positional information on the second-defect.

* * * * *